(12) United States Patent
Rioult et al.

(10) Patent No.: US 11,738,114 B2
(45) Date of Patent: *Aug. 29, 2023

(54) STERILIZATION OF SELF-ASSEMBLING PEPTIDES BY IRRADIATION

(71) Applicant: 3-D Matrix, Ltd., Cambridge, MA (US)

(72) Inventors: Marika G. Rioult, Cambridge, MA (US); Eun Seok Gil, Acton, MA (US); Elton Aleksi, West Roxbury, MA (US); Naoki Yamamoto, Hokuto (JP)

(73) Assignee: 3-D Matrix, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/074,244

(22) Filed: Dec. 2, 2022

(65) Prior Publication Data

US 2023/0149599 A1 May 18, 2023

Related U.S. Application Data

(62) Division of application No. 17/217,911, filed on Mar. 30, 2021, now Pat. No. 11,534,528.

(60) Provisional application No. 63/002,882, filed on Mar. 31, 2020.

(51) Int. Cl.
| | |
|---|---|
| *A61L 2/26* | (2006.01) |
| *C07K 7/08* | (2006.01) |
| *A61K 38/00* | (2006.01) |
| *A61L 27/22* | (2006.01) |
| *C12N 5/00* | (2006.01) |
| *A61L 2/08* | (2006.01) |
| *A61L 2/00* | (2006.01) |

(52) U.S. Cl.
CPC ......... *A61L 27/227* (2013.01); *A61L 2/0035* (2013.01); *A61L 2/081* (2013.01); *A61L 2/26* (2013.01); *C07K 7/08* (2013.01); *C12N 5/0068* (2013.01); *A61K 38/00* (2013.01)

(58) Field of Classification Search
CPC ...... A61L 27/227; A61L 2/0035; A61L 2/081; A61L 2/26; C07K 7/08; C12N 5/0068; A61K 38/00
See application file for complete search history.

(56) References Cited

U.S. PATENT DOCUMENTS

| | | | |
|---|---|---|---|
| 5,670,483 A | 9/1997 | Zhang et al. | |
| 5,955,343 A | 9/1999 | Holmes et al. | |
| 9,724,448 B2 | 8/2017 | Kobayashi et al. | |
| 10,369,237 B2 | 8/2019 | Gil et al. | |
| 10,596,225 B2 | 3/2020 | Takamura et al. | |
| 10,793,307 B2 | 10/2020 | Nohara et al. | |
| 2005/0129569 A1 | 6/2005 | Zhao et al. | |
| 2016/0287744 A1 | 10/2016 | Kobayashi et al. | |
| 2016/0317607 A1 | 11/2016 | Spirio et al. | |
| 2017/0128622 A1 | 5/2017 | Spirio et al. | |
| 2017/0173221 A1 | 6/2017 | Mehta et al. | |
| 2017/0202986 A1 | 7/2017 | Gil et al. | |
| 2019/0091376 A1 | 3/2019 | Kobayashi et al. | |
| 2019/0111165 A1 | 4/2019 | Gil et al. | |
| 2019/0358290 A1 | 11/2019 | Gil et al. | |
| 2020/0078489 A1 | 3/2020 | Kobayashi et al. | |
| 2021/0023257 A1 | 1/2021 | Kobayashi et al. | |

FOREIGN PATENT DOCUMENTS

| | | |
|---|---|---|
| WO | 2013133413 | 9/2013 |
| WO | 2014008400 | 1/2014 |
| WO | 2014133027 | 9/2014 |
| WO | 2014136081 | 9/2014 |
| WO | 2014141160 | 9/2014 |
| WO | 2015/136370 A2 * | 9/2015 |
| WO | 2015138473 | 9/2015 |
| WO | 2015138478 | 9/2015 |
| WO | 2015196020 | 12/2015 |

OTHER PUBLICATIONS

Gelain (Regenerative Medicine, pp. 1-8, 2021) (Year: 2021).*
Veira R et al, Peptide Structure Modifications: Effect of Radical Species Generated by Controlled Gamma Ray Irradiation Approach, Biol. Pharm. Bull. 2013, 36(4) 664-675.
Stadtman, E.R; Oxidation of free amino acids and amino acid residues in proteins by radiolysis and by metal-catalyzed reactions, Annu. Rev. Biochem., 62, 797-821 (1993).
International Search Report and Written Opinion for PCT/US2021/024954 dated Aug. 12, 2021.
Kang et al., The Influence of Electron Beam Sterilization on In Vivo Degradation of TCP/PCL of Different Composite Ratios for Bone Tissue Engineering, Micromachines. Mar. 6, 2020, vol. 11, No. 3, article 271, pp. 1-12; p. 3, para 3-4; p. 4, para 1; p. 6, para 3.

* cited by examiner

*Primary Examiner* — Alma Pipic
(74) *Attorney, Agent, or Firm* — IP Supra, PLLC; Constantine Linnik; Beth L. Smiley

(57) ABSTRACT

Gamma ray and e-beam irradiation provided efficient sterilization of certain self-assembling peptides (including RADA16 in solution) without substantial degradation of the major peptide, while, e.g., another self-assembly peptide, QLEL12 was significantly degraded following irradiation. Irradiation sterilization enhances the rheological property of, for example, RADA16 hydrogel once applied to tissue at a physiological pH. The rheological property increase can result in higher efficacy in a variety of biomedical applications.

12 Claims, 15 Drawing Sheets

Specification includes a Sequence Listing.

STERILIZATION OF SELF-ASSEMBLING PEPTIDES BY IRRADIATION

CONTINUITY

This application is a divisional of U.S. patent application Ser. No. 17/217,911, filed Mar. 30, 2021, which claims priority to U.S. provisional application No. 63/002,882, filed Mar. 31, 2020.

SEQUENCE LISTING

The instant application contains a XML Sequence Listing which is being submitted electronically and is hereby incorporated by reference in its entirety. Said Sequence Listing, created on Jan. 27, 2023 (EST), is named 3DM-20-01-IRR_US03-SLA.xml and is 32,737 bytes in size.

FIELD OF INVENTION

This invention relates to sterilization of certain medical gels, more specifically, gels containing so-called self-assembling peptides.

BACKGROUND OF THE INVENTION

Self-assembling peptides (sometimes abbreviated as "SAPs") are a type of peptides which assemble spontaneously into highly organized nanostructures when placed in aqueous environment and a chemical or physical change in surrounding conditions occur. One other well-known structure is a nanofibrous biopolymer structure formed by natural collagen. A class of SAPs relevant for this invention consists of alternating hydrophilic and hydrophobic amino acid residues capable of forming beta-sheets. They autonomously assemble into well-ordered nanostructures in neutral water, while they can temporarily disassemble into individual molecules when high shearing force is applied to them. SAPs can form a hydrogel (also known as SAP gels) depending on their environment such as pH and/or osmolality; for example, they are capable of forming a hydrogel when they are placed in the body at near neutral pH. SAP gels have been previously described as being used for a variety of medical applications, e.g., improved wound healing, inducement of homeostasis, reduction of adhesion in interior tissues, particularly, in context of surgery; as temporary tissue-void matrix fillers, facilitating ingrowth of natural tissue into such a void. Particular SAPs are described in U.S. Pat. Nos. 5,670,483; 5,955,343; 9,724,448; 10,596,225 and Int'l Pat. Appln. Pub. WO2014/136081; and foreign equivalents thereof.

Sterilization is a very important step in the manufacturing process for most biomaterials, including for self-assembling peptide solutions. PuraStat® (RADA16=Ac-RADARA-DARADARADA-NH$_2$=SEQ ID NO:1; about 2.5%) is customarily filtered for sterilization (see, e.g., Int'l. Pat. Appln. Pub. No. WO 2014/008400); however, PuraStat®'s viscosity at higher concentrations is the main obstacle to its filtration, which, in addition to losses in the tubing, results in substantial peptide losses. In this method for sterilizing, a solution of SAPs is forced through a porous filter, wherein the sterilizing filter has an average pore size of 0.22 μm (US Pat. Appln. No. 2015/019735). As another method, some thermally stable self-assembling peptide solutions can be sterilized by autoclaving treatment at about 121° C. for about 25 minutes (U.S. patent application Ser. No. 10/369,237).

Furthermore, an additional ethylene oxide sterilization step is required for the outer part of PuraStat® products. And, it was discovered that autoclaving cannot be used for some SAPs, such as RADA16 (SEQ ID NO:1) in solution, because of its complete thermal degradation (US Pat. Appln. Pub. No. 2017/0202986). Thus, another new sterilization method has been needed to reduce losses, particularly, for RADA16 (SEQ ID NO:1) and other SAPs.

Gamma irradiation sterilization of self-assembling peptides including RADA16 (SEQ ID NO:1) was described in passing in a prior publication (US Pat. Appln. Pub. No. 2016/0317607; at paragraph [0052]); but no specific conditions or actual effect of irradiation on the structure and properties of self-assembling peptides, including RADA16 (SEQ ID NO:1), have been described so far. In fact, peptide structure can be changed by the reactive radical species generated by irradiation such as gamma ray, X-ray, and e-beam. Such a structural change can be governed by multiple factors including the amino acid composition, reactive residue position and possibly the conformation acquired by each macromolecule (Vieira R et al, Biol. Pharm. Bull. 2013, 36(4) 664-675). For example, regardless of the different sequences of the peptides in that article, all the tested nine peptides showed a progressive degradation by gamma ray irradiation up to 15 kGy. Considering that even higher doses of irradiation than 15 kGy may be required for sterilization processes, numerous peptides cannot be sterilized with gamma ray irradiation without substantial degradation. It is well known that the side chains of aromatic amino acids (i.e., Phenylalanine (F), Tyrosine (Y), Tryptophan (W), Histidine (H), and Proline (P)) and sulfur-containing amino acids (i.e., Cysteine (C)) are especially weak to attack by reactive radical species (Annu. Rev. Biochem., 62, 797-821 (1993) and Vieira R et al, Biol. Pharm. Bull. 2013, 36(4) 664-675). By way of background, the followings SAPs, RADA16 (Ac-RADARADARA-DARADA-NH$_2$ (SEQ ID NO:1)), KLD12 (Ac-KLDLKLD-LKLDL-NH$_2$ (SEQ ID NO:2)), and IEIK13 (Ac-IEIKIEIK-IEIKI-NH$_2$ (SEQ ID NO:3)), do not include aromatic amino acids or sulfur-containing amino acids.

On the other hand, irradiation sterilization can also affect the secondary structure of self-assembling peptides and their fibrous structure. As mentioned, RADA16 (SEQ ID NO:1), KLD12 (SEQ ID NO:2) and IEIK13 (SEQ ID NO:3) have beta-sheet conformation, and these molecules self-assemble to form an ordered nanofibrous structure. The irradiation sterilization process may potentially change the secondary structure and the nanofiber structure of peptide, which could then result in the undesirable change of its rheological properties.

Thus, there exists a need for new sterilization methods that work advantageously with self-assembling peptides. For the reasons cited above, sterilization by irradiation has been avoided so far.

SUMMARY OF THE INVENTION

Figure 1A:
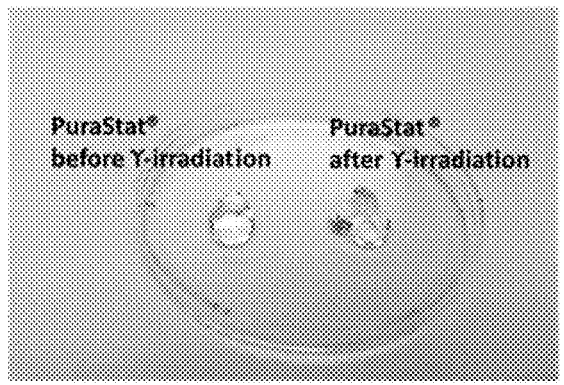
FIG. 1A shows the appearance of PuraStat® (RADA16 (SEQ ID NO:1) 2.5%) and IEIK13 (SEQ ID NO:3) 1.3% before gamma-irradiation.

In the present disclosure, the effect of sterilization by irradiation on self-assembling peptide solutions was evaluated, specifically, with the following peptides: PuraStat® (Ac-RADARADARADARADA-NH$_2$, RADA16 (SEQ ID NO:1), IEIK13 (Ac-IEIKIEIKIEIKI-NH$_2$ (SEQ ID NO:3)), and QLEL12 (Ac-QLELQLELQLEL-NH$_2$ (SEQ ID NO:4)). It was unexpectedly found that gamma-irradiation sterilization enhanced the rheological properties of certain self-assembling peptide solutions and hydrogels without the anticipated noteworthy degradation, while certain other peptides showed the expected significant degradation and viscosity drop after gamma irradiation (i.e., unlike RADA16 (SEQ ID NO:1) and IEIK13 (SEQ ID NO:3)), while, e.g., another self-assembling peptide, QLEL12 (Ac-QLELQLELQLEL-NH$_2$ (SEQ ID NO:4)) was significantly degraded following irradiation. This invention is further based on the prophetic finding that the same result can be expected with other similar irradiation sterilization methods including, specifically, X-ray and e-beam, at least for the respective peptides. Thus, in some embodiments, the method of sterilizing a self-assembling peptide solution comprises:

a) placing one or more containers with a solution of self-assembling peptide into an irradiation machine, said self-assembling peptide capable of forming a hydrogel when applied to a biological tissue at about neutral pH; and b) exposing the container to gamma ray, X-ray and/or e-beam irradiation at a predetermined dose so that the peptide solution is sterilized without substantial degradation of the peptide while its desired biological and/or rheological property(ies) is/are maintained at the same level or improved.

In some embodiments, the peptides are selected from the group consisting of RADA16 (SEQ ID NO:1), KLD12 (SEQ ID NO:2), and IEIK13 (SEQ ID NO:3). In related embodiments, such peptides are exposed to the dose is 15-50 kGy, preferably 15-40 kGy, more preferably, to a minimum dose resulting in a desired sterility assurance level (SAL), without substantial degradation and/or substantial negative change in biological properties of these peptides. In some embodiments, the peptide solution is irradiated by gamma-rays, X-rays, or e-beam. In some embodiments, the over-all degradation of the total peptides in solution after irradiation does not exceed 20%, more preferably, 10%, most preferably 5%, of the amount of peptides prior to irradiation. In some embodiments, the desired biological or physical property(ies) is/are selected from the group consisting of: hemostatic, anti-adhesion, prevention of re-bleeding, anti-stenosis, tissue occlusion, storage modulus (e.g., in some embodiments, the storage modulus of the gelled solution is increased at least by 10%, at least by 15% or at least by 20% post-irradiation, and viscosity, and tissue void filling property are maintained within acceptable or improved parameters after irradiation. In some embodiments, irradiation dose achieves sterility assurance level (SAL) of at least $10^{-5}$, preferably $10^{-6}$, or less. In other embodiments, using the bioburden testing described below in the example, the acceptable level of contamination of the peptide solution pre-irradiation is 1000, 500, 100, 15, 10, 9, 5, 2, 1.5, 1 CFU, or less. In some embodiments, the concentration of the degradation products of the intact ("major" or "full-length") peptide in the solution post-irradiation ranges from 0.1% to 5%. In some embodiments, the pH of the peptide solution post-irradiation ranges from about 1.8 to 3.5. In some embodiments, the solution container is a plastic syringe, with or without an adapter nozzle. In such embodiments, care is taken to ensure that the plastic and rubber parts of the packaging also maintain their desired physical properties. While some yellowing of the plastic syringes may be expected and is normal, any rubberized material must preserve its e plastic properties at an acceptable level.

In some embodiments, the gelled solution is further subjected to sheering to reduce or restore its storage modulus.

Thus, the invention provides a sterilization method for self-assembling peptides. According to the methods of the invention, in some embodiments, the solution is further applied to a biological tissue, for example, during surgery, or after trauma involving bleeding.

DETAILED DESCRIPTION OF THE INVENTION

As stated above, in the present disclosure, the effect of sterilization by irradiation on self-assembling peptide solutions was evaluated, specifically, with the following peptides: PuraStat® (Ac-RADARADARADARADA-NH$_2$ (SEQ ID NO:1); RADA16), IEIK13 (Ac-IEIKIEIKIEIKI-NH$_2$ (SEQ ID NO:3)), and QLEL12 (Ac-QLELQLELQLEL-NH$_2$ (SEQ ID NO:4)). In some embodiments, the method of sterilizing a self-assembling peptide solution comprises:

a) placing one or more containers with a solution of self-assembling peptide into an irradiation machine, said self-assembling peptide capable of forming a hydrogel when applied to a biological tissue (e.g., in situ) at about neutral pH; and b) exposing the container to gamma ray, X-ray and/or e-beam irradiation at a predetermined dose so that the peptide solution is sterilized to a pre-determined Sterility Assurance Level (SAL) without substantial degradation of the peptide while its desired biological and/or physical property(ies) is/are maintained substantially at the same level or improved.

It was unexpectedly found that gamma-irradiation sterilization enhanced the rheological properties of certain self-assembling peptide solutions and hydrogels without causing any noteworthy degradation, while certain other peptides showed significant degradation and viscosity drop after gamma irradiation, i.e., unlike RADA16 (SEQ ID NO:1) and IEIK13 (SEQ ID NO:3), another self-assembling peptide, QLEL12 (Ac-QLELQLELQLEL-NH$_2$ (SEQ ID NO:4)) was significantly degraded following irradiation.

This invention is further based on the prophetic finding that the same result can be expected with other similar irradiation sterilization methods including, specifically, X-ray and e-beam, at least for the respective peptides. In preferred embodiments, the composition and methods of the invention maintain or improve the desired biological property(ies) such as hemostatic, anti-adhesion, prevention of re-bleeding, anti-stenosis, tissue occlusion, storage modulus, viscosity, and tissue void filling property, etc. For example, in some embodiments, the storage modulus in increased by at least 5%, 10%, 15%, 20%, or more. If such increase is undesirable for certain applications, the gel can be thinned further by dilution or sheering by methods known in the art, turning it into the solution or otherwise reducing its storage modulus. In certain embodiments, the irradiated solution of SAPs remains clear and viscous.

In some embodiments, the SAPs comprise a sequence of amino acid residues conforming to one or more of Formulas I-IV:

$$((Xaa^{neu}-Xaa^+)_x(Xaa^{neu}-Xaa^-)_y)_n \quad (I)$$

$$((Xaa^{neu}-Xaa^-)_x(Xaa^{neu}-Xaa^+)_y)_n \quad (II)$$

$$((Xaa^+-Xaa^{neu})_x(Xaa^--Xaa^{neu})_y)_n \quad (III)$$

$$((Xaa^--Xaa^{neu})_x(Xaa^+-Xaa^{neu})_y)_n \quad (IV)$$

$Xaa^{neu}$ represents an amino acid residue having a neutral charge; $Xaa^+$ represents an amino acid residue having a positive charge; $Xaa^-$ represents an amino acid residue having a negative charge; x and y are integers having a value of 1, 2, 3, or 4, independently; and n is an integer having a value of 1-5.

In some embodiments, the SAPs further comprise an amino acid sequence that interacts with the extracellular matrix, wherein the amino acid sequence anchors the SAPs to the extracellular matrix.

In some embodiments, the amino acid residues in the SAPs can be naturally occurring or non-naturally occurring amino acid residues. Naturally occurring amino acids can include amino acid residues encoded by the standard genetic code as well as non-standard amino acids (e.g., amino acids having the D-configuration instead of the L-configuration), as well as those amino acids that can be formed by modifications of standard amino acids (e.g., pyrolysine or selenocysteine). Suitable non-naturally occurring amino acids include, but are not limited to, D-alloisoleucine(2R,3S)-2-amino-3-methylpentanoic acid, L-cyclopentyl glycine (S)-2-amino-2-cyclopentyl acetic acid.

In other embodiments, another class of materials that can self-assemble are peptidomimetics. Peptidomimetics, as used herein, refers to molecules which mimic peptide structure. Peptidomimetics have general features analogous to their parent structures, polypeptides, such as amphiphilicity. Examples of such peptidomimetic materials are described in Moore et al., Chem. Rev. 101(12), 3893-4012 (2001). The peptidomimetic materials can be classified into four categories: α-peptides, β-peptides, γ-peptides, and δ-peptides. Copolymers of these peptides can also be used. Examples of α-peptide peptidomimetics include, but are not limited to, N,N'-linked oligoureas, oligopyrrolinones, oxazolidin-2-ones, azatides and azapeptides. Examples of β-peptides include, but are not limited to, β-peptide foldamers, α-aminoxy acids, sulfur-containing β-peptide analogues, and hydrazino peptides. Examples of γ-peptides include, but are not limited to, γ-peptide foldamers, oligoureas, oligocarbamates, and phosphodiesters. Examples of δ-peptides include, but are not limited to, alkene-based δ-amino acids and carbopeptoids, such as pyranose-based carbopeptoids and furanose-based carbopeptoids.

In certain embodiments, the SAP is AC5®, AC5-V®, AC5-G™ or TK45, also known as AC1, made by Arch Therapeutics, Inc. (see www.archtherapeutics.com).

In some embodiments, the SAP solution is contained in "storage and/or drug delivery system", such as, for example, storage and/or delivery systems suitable for peptide compositions described herein, for example, vials, bottles, beakers, bags, syringes, ampules, cartridges, reservoirs, or LYO-JECTS®. Storage and/or delivery systems need not be one in the same and can be separate. In specific embodiments, SAPs are provided in a plastic syringe, containing about 10 ml, about 7.5 ml, about 5, about 2.5, about 1, or about 0.5 ml of a SAP solution. In certain embodiments, the plastics (e.g., plastic syringe) may acquire a yellowish tint after irradiation, which is normal, and does not affect biomedical characteristics of the therein contained SAP Solution In some embodiments, such storage and delivery system may further contain a "nozzle" which refers to a generally thin, cylindrical object, often with a narrow end and a wide end, which is adapted for fixing onto a delivery device described herein. In some embodiments, the terms "nozzle" and "cannula" are used interchangeably. Nozzles are composed of two connection points or ends, a first connection point or end to connect to a delivery system (e.g., a syringe) and a second connection point which may serve as the point where delivery of pharmaceutical composition is administered or as a point to connect to a secondary device (e.g., a catheter).

Thus, the invention provides methods of making sterilized solutions of the self-assembling peptides. The invention also provides use of such sterilized solutions applied to a biological tissue, e.g., in situ, for example, during surgery or after trauma involving bleeding, or use of so-sterilized solutions in treatment or prevention of other diseases or conditions; for example, as described in as described in Int'l Pat. Appln. WO2014/133027, or as described in US Pat. Appln. Pub. Nos. 2011/02101541 and occlude a site of tissue damage; or as described US Pat. Appln. Pub. No. 2016/0287744 for vascular embolization; or as described in U.S. patent application Ser. No. 16/085,803 for occlusion of cerebrospinal fluid leakage, or as described in Int'l Pat. Pub. Appln. No. WO2013/133414 as mucosa elevating agent; or as described in Int'l Pat. Pub. Appln. No. WO2014/141160 for bile leakage occlusion; or as described in U.S. patent application Ser. No. 16/885,753 for anti-adhesion of tissues; or as described in U.S. patent application Ser. No. 16/085,804 for pancreatic fistula occlusion; or as described in U.S. patent application Ser. No. 15/124,639 for bronchial obstruction; or as described in Int'l Pat. Appln. Pub. No. WO2015/138,478 for treating pulmonary bulla collapse; or as described in Int'l Pat. Appln. Pub. No. WO2015/019,738 for treatment of pulmonary leakage; or as described in Int'l Pat. Appln. Pub. No. WO2015/196020 for filling dental bone voids; or as described US Pat. Appln. Pub. No. 2017/0128622 for filling bone voids; or as described in U.S. patent application Ser. No. 16/312,878 for the prevention of esophageal structure after endoscopic dissection, and foreign equivalents of any of the aforementioned publications, and other methods known in the art. Accordingly, in some embodiments, the invention provides the use of a sterilized solution of the self-assembling peptide for treating or preventing an aforementioned disease or condition, wherein the sterilized solution is obtained by the methods of the invention. In certain such embodiments, the self-assembling peptide solution exhibits a post-irradiation mass spectrometric (MS) profile substantially as shown in corresponding post-irradiation profiles of FIGS. 2-6 and/or as described in the Examples. For example, in the case of PuraStat®, the additional major $M_z$ peaks at are observed at 836/1670, 1100, and 1513 m/z.

An average bioburden <1,000 CFU is the typical sterility of PuraStat® before sterilization. In this case, to achieve a sterility assurance level, SAL, of $10^{-6}$, the range of irradiation dose should be between 25 kGy and 40 kGy. With gamma and X-ray methods, about up to 20% of the over-all peptides may degrade during sterilization process. With e-beam method, about up to 10% of the over-all peptides may degrade during sterilization process. PuraStat® rheology increases after sterilization by gamma-ray, or X-ray, which can alter its hemostatic efficacy positively or negatively. However, PuraStat® rheology does not change after e-beam sterilization.

In certain embodiments, using the bioburden testing described below in the Examples, the acceptable level of contamination of the peptide solution pre-irradiation may be <1000, <500, <100, <15, <10, <9, <5, <2, <1.5, <1 CFU, or less per product unit. The preferred bioburden pre-sterilization is <9 CFU. Thus, under 9 CFU, the range of irradiation dose can be selected between 15 kGy and 24 kGy. While the low end of the irradiation dose range may be determined by the bioburden of the pre-irradiated product, the high end of the range is chosen based on the configuration and choice of the irradiator machine and set at a minimum required to achieve desirable sterility assurance level (SAL).

With gamma and X-ray methods, up to 10% of the peptides may degrade during sterilization process. With e-beam method, the peptides may not significantly degrade during sterilization process. Even in this case, PuraStat® rheology increases after gamma-ray and X-ray sterilization, which may somewhat change its hemostatic efficacy positively or negatively. Thus, PuraStat® rheology does not change after e-beam sterilization and thus may be preferred, if no or minimal change in rheological properties and its hemostatic properties is desirable. Therefore, e-beam irradiation may be particularly preferred for PuraStat®.

In some embodiments, the concentration of degraded full-length peptide ("major peptide") in the solution post-irradiation ranges from 0.1% to 5%, 0.1% to 4%, 0.1% to 3%, 0.1% to 2.5%, 0.1% to 2%, or 0.1% or 1.5% or less. In some embodiments, for RADA16 (SEQ ID NO:1), KLD12 (SEQ ID NO:2), or IEIK13 (SEQ ID NO:3) solution irradiated with a total dose, which may depend on its pre-irradiation bioburden, including, for example, 15-50 kGy, 25 kGy+/−15 kGy, 40 kGy-10 kGy, 35 kGy-10 kGy, 30 kGy-10 kGy, 15 kGy-24 KGy, 25 kGy-10 kGy, 20 kGy-10 kGy, 10 kGy-15 kGy, and 12 kGy-14 kGy. Doses around 12-14 kGy appear to be optimal for gamma irradiation, however, the peptide solution may also be irradiated with similar doses with X-ray or e-beam.

In some embodiments, the "storage and/or drug delivery system", for example, a plastic syringe contained in a blister pack, is irradiated in batches of at least: 100, 200, 300, 400, 500, 600, 700, 800, 900, 1000, 2,000, 3,000, 4,000, 5,000, 6,000, 7,000, 8,000, 9,000, 10,000 units or more at a time. Generally, it is preferred that the total exposure of any sample in an irradiated batch does not exceed 100 kGy, more preferably 60 kGy, most preferably, 50 kGy, or less as described herein.

In some embodiments, the major peptide's degradation (also referred to as "full-length peptide's degradation") after the irradiation does not exceed 20% of the amount of the peptide prior to the irradiation and, preferably, does not exceed 18%, 16%, 14%, 12%, 10%, 8%, 5%, 3%, or 1%. In some embodiments, the total dose is achieved over a period of time sufficient to achieve necessary sterility of the solution. For example, the dose of 40 kGy can be delivered by radiation intensity 6.3 kGy/hr for about 6 hrs and 21 min. Other combinations can be found in Example 1. In some embodiments, a constant dose was delivered over a number of hours, e.g., about 10, about 9, about 8, about 7, about 6, about 5, about 4, about 3, or about 2 hours.

In some embodiments, samples are irradiated with gamma ray doses, for example, of about 23, about 25, about 28 or about 40 kGy, or other doses indicated above with an instrument, for example, such as Gammacell 220® High Dose Rate Co-60 Irradiator in VPTrad (www.vptrad.com; MDS Nordion, Ottawa, Canada).

In other embodiments, samples are irradiated with X-ray with doses of about 25 kGy to about 40 kGy, or the doses as indicated above, with a Mevex accelerator (with the following settings: 10 MeV, 20 kW).

In general, X-ray frequency range is $3 \times 10^{16}$-$3 \times 10^{19}$ Hz, while the frequency range of gamma-rays is $3 \times 10^{19}$ or higher.

In other embodiments, samples are irradiated with e-beam at about 25 to about 40 kGy with a Mevex accelerator (with the following settings: 10 MeV, 20 kW) (see mevex.com/linacs/10mev-system-e-beam-sterilization-for-medical-devices/).

In some embodiments, the desired biological and physical property(ies) is/are selected from the group consisting of: hemostatic, anti-adhesion, prevention of re-bleeding, anti-stenosis, tissue occlusion, storage modulus, viscosity, tissue void filling property, mucosa elevation, and wound healing, In preferred embodiments, the irradiation dose achieves a sterility assurance level (SAL) of at least $10^{-5}$, $10^{-6}$, or less.

The invention also provides the sterilized solution of self-assembling peptide made by the methods described herein. Such comprising: applying the solution to a biological tissue, for example, during surgery or after trauma involving bleeding, to a site with substantially neutral pH, resulting in gelling. In some embodiments, such site is internal, while in other embodiment the site can be external such surface sutures, cuts, or scrapes.

Other aspects of the invention would be apparent to those of skill in the art based on the present description, including the Examples and the appended claims.

Example 1: Irradiation Conditions

Samples were irradiated with gamma rays at 23, 25, 28 and 40 kGy with VPTrad Gammacell 220® High Dose Rate Co-60 Irradiator. In some embodiments, the run dose rate and duration time for 40 kGy irradiation were 6.30 kGy/hr and 6 hours 20 minutes 58 seconds, respectively. In other embodiments, the run dose rate and duration time for 28 kGy irradiation were 4.40 kGy/hr and 6 hours 22 minutes 31 seconds, respectively. In other embodiments, the run dose rate and duration time for 25 kGy irradiation were 6.58 kGy/hr and 3 hours 47 minutes 42 seconds, respectively. In other embodiments, the run dose rate and duration time for 23 kGy irradiation were 6.58 kGy/hr and 3 hours 29 minutes 29 seconds, respectively.

In other embodiments, samples were irradiated with X-ray at 25 kGy and 40 kGy with a Mevex accelerator (10 MeV, 20 kW).

In other embodiments, samples were irradiated with e-beam at 25 and 40 kGy with a Mevex accelerator (10 MeV, 20 kW).

Example 2: HPLC Conditions

HPLC tests were performed to evaluate the major peptide content after irradiation tests. An Agilent HPLC 1100 (Agilent Technologies) was used for this study. The column temperature was kept at 25° C.

For RADA16 (SEQ ID NO:1) samples, solvent A was water with 0.1% TFA and solvent B was 80% acetonitrile with 0.1% TFA. Gradient of solvent B was controlled from 10% to 40% in 20 min and 40% for another 5 min at 25° C. Agilent Zorbax 300SB-C18 column (4.6 mm×250 mm, 5 m, 300 Å) was used for this test. PuraStat® (RADA16 (SEQ ID NO:1) 2.5%) (40 mg) was mixed with 10 µL of DH$_2$O and the mixture was vortexed. The mixture was further mixed with 500 µL of formic acid and vortexed. This mixture was then mixed with DH$_2$O (4,450 µL) and vortexed. 20 µL samples were injected using an Agilent autosampler.

For IEIK13 (SEQ ID NO:3) samples, solvent A was water with 0.1% TFA and solvent B was 90% Acetonitrile with 0.1% TFA. The gradient of solvent B was controlled from 20% to 43% in 8 min, from 43% to 70% between 8 and 9.5 min, and from 70% to 95% between 9.5 and 30 min, and 95% for another 5 min at 25° C. An Agilent PLRP-S column (4.6 mm×250 mm, 8 m, 300 Å) was used for this test. A 1.3% solution of IEIK13 (SEQ ID NO:3) was diluted with water with 0.1% TFA to 0.075% and the mixture was vortexed. 35 µL samples were injected using an Agilent autosampler.

For QLEL12 (SEQ ID NO:4) samples, solvent A was water and solvent B was 80% acetonitrile. The gradient of solvent B was controlled from 20% to 80% in 15 min and 80% for another 7 min at 25° C. An Agilent PLRP-S column (4.6 mm×250 mm, 8 m, 300 Å) was used for this test. 0.15% w/v of QLEL12 (SEQ ID NO:4) solution was diluted to 0.01% with DH$_2$O and vortexed. 50 µL samples were injected using an Agilent autosampler.

Example 3: Mass Spectrometry Conditions

Mass spectrometry tests were carried out to investigate the degradation of the peptides after irradiation sterilization. An Agilent LC/MSD ion trap mass spectrometer was used for this study. The sample solutions were prepared as described above for the HPLC samples. Each sample was injected at 9 µL/min with a syringe pump. Each mass spectrum was recorded for 1 minute.

Example 4: Rheological Properties of Irradiated Self-Assembling Peptides

The rheological properties of samples were evaluated using a rheometer (DHR1, TA Instruments) with 40 mm cone and plate. Peptide solution (700 µL) was placed on the rheometer plate and excess solution was gently removed by a metal spatula. Measurements were performed after 2 minutes of relaxation time at 37° C.

Frequency tests were performed at 0.1% of strain from 0.1 Hz to 10 Hz. Frequency tests after gelation were performed under the same conditions for 20 minutes after 3 mL of DMEM was gently added around the cone and the plate.

Thixotropic tests were carried out with the following method. A shear rate of 1000 s$^{-1}$ was applied for 1 minute to reset all rheological properties. Then 1 Hz of frequency at 0.1% of strain was applied for 60 minutes to record thixotropic behaviors. This sequence was repeated, and the thixotropic properties were then analyzed.

Example 5: Appearance and pH

Figure 1B:
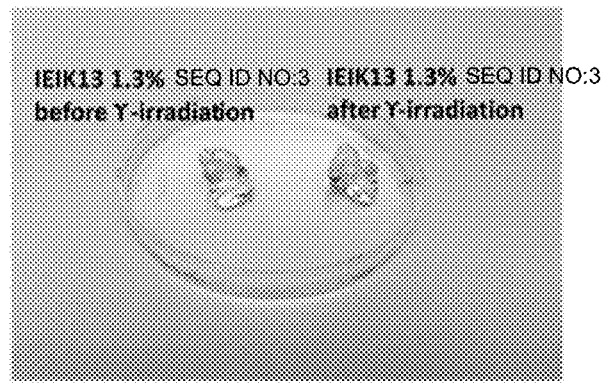
FIG. 1B shows the appearance of PuraStat® (RADA16 (SEQ ID NO:1) 2.5%) and IEIK13 (SEQ ID NO:3) 1.3% after gamma-irradiation at 28 kGy.

The appearance and pH of PuraStat® after gamma irradiation are shown in FIG. 1 and Table 1 (N=3).

TABLE 1

| Appearance and pH of PuraStat ® (RADA16 (SEQ ID NO: 1) 2.5%) after gamma irradiation. | | |
|---|---|---|
| Testing conditions | Appearance | pH |
| PuraStat ® control | Clear and viscous | 2.2 |
| PuraStat ® irradiated (gamma) at 23 kGy | Clear and viscous | 2.3 |
| PuraStat ® irradiated (gamma) at 25 kGy | Clear and viscous | 2.3 |
| PuraStat ® irradiated (gamma) at 28 kGy | Clear and viscous | 2.3 |
| PuraStat ® irradiated (gamma) at 40 kGy | Clear and viscous | 2.3 |

The appearance and pH of PuraStat® after gamma irradiation were only slightly altered. The pH of the PuraStat® control was 2.2. The pH of PuraStat® after gamma irradiation at 23, 25, 28, and 40 kGy were 2.3.

The appearance and pH of IEIK13 (SEQ ID NO:3) 1.3% after gamma irradiation are also shown in FIG. 1 and Table 2.

TABLE 2

Appearance and pH of IEIK13 (SEQ ID NO: 3) 1.3%, KLD12 (SEQ ID NO: 2) 1.3% and QLEL12 (SEQ ID NO: 4) 0.15% after gamma irradiation. (N = 3)

| Testing conditions | Appearance | pH |
| --- | --- | --- |
| IEIK13 (SEQ ID NO: 3) control | Clear and viscous | 3.0 |
| IEIK13 (SEQ ID NO: 3) irradiated (gamma) at 28 kGy | Clear and viscous | 3.0 |
| IEIK13 (SEQ ID NO: 3) irradiated (gamma) at 40 kGy | Clear and viscous | 3.0 |
| KLD12 (SEQ ID NO: 2) control | Clear and viscous | 2.2 |
| KLD12 (SEQ ID NO: 2) irradiated (gamma) at 40 kGy | Clear and viscous | 2.2 |
| QLEL12 (SEQ ID NO: 4) control | Clear and viscous | 7.0 |
| QLEL12 (SEQ ID NO: 4) irradiated (gamma) at 23 kGy | Clear and watery | 6.7 |
| QLEL12 (SEQ ID NO: 4) irradiated (gamma) at 25 kGy | Clear and watery | 6.5 |
| QLEL12 (SEQ ID NO: 4) irradiated (gamma) at 40 kGy | Clear and watery | 5.9 |

The appearance and pH of IEIK13 (SEQ ID NO:3) (1.3%) after gamma irradiation were not changed. The pH of IEIK13 (SEQ ID NO:3) control was 3.0. The pH of IEIK13 (SEQ ID NO:3) (1.3%) after gamma irradiation at 28 kGy and at 40 kGy was 3.0.

The appearance and pH of KLD12 (SEQ ID NO:2) (1.3%) and QLEL12 (SEQ ID NO:4) (0.15%) after gamma irradiation were also shown in Table 2. The appearance and pH of KLD12 (SEQ ID NO:2) (1.3%) after gamma irradiation were not changed. The pH of KLD12 (SEQ ID NO:2) control was 2.2. The pH of KLD12 (SEQ ID NO:2) (1.3%) after gamma irradiation at 40 kGy were 2.2.

However, the appearance and pH of QLEL12 (SEQ ID NO:4) after gamma irradiation were significantly altered. The pH of the QLEL12 (SEQ ID NO:4) control was 7.0. The pH of QLEL12 (SEQ ID NO:4) after gamma irradiation at 23, 25 and 40 kGy were 6.7, 6.5 and 5.9, respectively, and the samples became watery after gamma irradiation.

The appearance and pH of PuraStat® after X-ray and e-beam irradiation are also shown in Table 3 (N=3).

TABLE 3

Appearance and pH of PuraStat ® (RADA16 (SEQ ID NO: 1) 2.5%) after X-ray and e-beam irradiation test. (N = 3)

| Testing conditions | Appearance | pH |
| --- | --- | --- |
| PuraStat ® control | Clear and viscous | 2.2 |
| PuraStat ® irradiated (X-ray) at 25 kGy | Clear and viscous | 2.3 |
| PuraStat ® irradiated (X-ray) at 40 kGy | Clear and viscous | 2.3 |
| PuraStat ® irradiated (e-beam) at 25 kGy | Clear and viscous | 2.2 |
| PuraStat ® irradiated (e-beam) at 40 kGy | Clear and viscous | 2.2 |

The appearance and pH of PuraStat® after X-ray or e-beam irradiation was only slightly changed or remained unchanged. The pH of PuraStat® control was 2.2. The pH of PuraStat® after X-ray irradiation at 25 kGy and at 40 kGy was 2.3. The pH of PuraStat® after e-beam irradiation at 25 kGy and at 40 kGy was 2.2.

The appearance and pH of IEIK13 (SEQ ID NO: 3) 1.3% after X-ray or e-beam irradiation are also shown in Table 4.

TABLE 4

Appearance and pH of IEIK13 (SEQ ID NO: 3) 1.3% after X-ray or e-beam irradiation (N = 3).

| Testing conditions | Appearance | pH |
| --- | --- | --- |
| IEIK13 (SEQ ID NO: 3) control | Clear and viscous | 3.0 |
| IEIK13 (SEQ ID NO: 3) irradiated (X-ray) at 25 kGy | Clear and viscous | 3.0 |
| IEIK13 (SEQ ID NO: 3) irradiated (X-ray) at 40 kGy | Clear and viscous | 3.0 |
| IEIK13 (SEQ ID NO: 3) irradiated (e-beam) at 25 kGy | Clear and viscous | 3.0 |
| IEIK13 (SEQ ID NO: 3) irradiated (e-beam) at 40 kGy | Clear and viscous | 3.0 |

The appearance and pH of IEIK13 (SEQ ID NO:3) 1.3% after X-ray or e-beam irradiation were not changed. The pH of IEIK13 (SEQ ID NO:3) 1.3% control was 3.0. The pH of IEIK13 (SEQ ID NO:3) 1.3% after X-ray or e-beam irradiation at 28 kGy and 40 kGy were 3.0.

The appearance and pH of KLD12 (SEQ ID NO:2) 1.3% after X-ray or e-beam irradiation are also shown in Table 5.

TABLE 5

Appearance and pH of KLD12 (SEQ ID NO: 2) 1.3% after X-ray or e-beam irradiation (N = 3).

| Testing conditions | Appearance | pH |
| --- | --- | --- |
| KLD12 (SEQ ID NO: 2) control | Clear and viscous | 2.2 |
| KLD12 (SEQ ID NO: 2) irradiated (X-ray) at 25 kGy | Clear and viscous | 2.2 |
| KLD12 (SEQ ID NO: 2) irradiated (X-ray) at 40 kGy | Clear and viscous | 2.2 |
| KLD12 (SEQ ID NO: 2) irradiated (e-beam) at 25 kGy | Clear and viscous | 2.2 |
| KLD12 (SEQ ID NO: 2) irradiated (e-beam) at 40 kGy | Clear and viscous | 2.2 |

The appearance and pH of KLD12 (SEQ ID NO:2) 1.3% after X-ray or e-beam irradiation were not changed. The pH of KLD12 (SEQ ID NO:2) 1.3% control was 2.2. The pH of KLD12 (SEQ ID NO:2) 1.3% after X-ray or e-beam irradiation at 25 kGy and 40 kGy was 2.2.

The appearance and pH of QLEL12 (SEQ ID NO:4) 0.15% after X-ray or e-beam irradiation are also shown in Table 6.

TABLE 6

Appearance and pH of QLEL12 (SEQ ID NO: 4) 0.15% after X-ray and e-beam irradiation (N = 3).

| Testing conditions | Appearance | pH |
| --- | --- | --- |
| QLEL12 (SEQ ID NO: 4) control | Clear and viscous | 7.0 |
| QLEL12 (SEQ ID NO: 4) irradiated (Gamma) at 25 kGy | Clear and watery | 6.5 |
| QLEL12 (SEQ ID NO: 4) irradiated (Gamma) at 40 kGy | Clear and watery | 5.9 |
| QLEL12 (SEQ ID NO: 4) irradiated (X-ray) at 25 kGy | Clear and watery | 6.3 |
| QLEL12 (SEQ ID NO: 4) irradiated (X-ray) at 40 kGy | Clear and watery | 5.9 |
| QLEL12 (SEQ ID NO: 4) irradiated (e-beam) at 25 kGy | Clear and watery | 6.6 |
| QLEL12 (SEQ ID NO: 4) irradiated (e-beam) at 40 kGy | Clear and watery | 6.5 |

The appearance of QLEL12 (SEQ ID NO:4) after gamma, X-ray or e-beam irradiation was significantly altered. The pH of the QLEL12 (SEQ ID NO:4) control was 7.0. The pH's of QLEL12 (SEQ ID NO:4) after gamma irradiation at 25 and 40 kGy were 6.5 and 5.9, respectively, those after X-ray irradiation at 25 and 40 kGy were 6.3 and 6.5, respectively, and those after e-beam irradiation at 25 and 40 kGy were 6.6 and 6.5, respectively. QLEL12 (SEQ ID NO:4) solutions became watery after gamma, X-ray or e-beam irradiation.

In summary, RADA16 (SEQ ID NO:1), IEIK13 (SEQ ID NO:3) and KLD12 (SEQ ID NO:2) remained unchanged after gamma, X-ray and e-beam irradiation at around 25~40 kGy, but QLEL12 (SEQ ID NO:4) was changed. Therefore, unlike QLEL12 (SEQ ID NO:4), RADA16 (SEQ ID NO:1), IEIK13 (SEQ ID NO:3), and KLD12 (SEQ ID NO:2) can be sterilized using a gamma, X-ray and e-beam irradiation techniques.

Example 6: Characterization by HPLC and Mass Spectrometry

The HPLC tests for RADA16 (SEQ ID NO:1), IEIK13 (SEQ ID NO:3), and QLEL12 (SEQ ID NO:4) were performed before and after gamma, X-ray and e-beam irradiation, and the results for their major peptide content are listed in Tables 7-10.

TABLE 7

HPLC test for major peptide content of PuraStat ® (RADA16 (SEQ ID NO: 1) 2.5%) before and after gamma-irradiation (N = 3, mean ± SD).

| Testing conditions | Major peptide content (%) |
|---|---|
| PuraStat ® control | 78.3 ± 1.7 |
| PuraStat ® irradiated (gamma) at 23 kGy | 75.5 ± 1.4* |
| PuraStat ® irradiated (gamma) at 25 kGy | 74.6 ± 0.7* |
| PuraStat ® irradiated (gamma) at 28 kGy | 68.5 ± 0.5* |
| PuraStat ® irradiated (gamma) at 40 kGy | 69.7 ± 0.5* |

*denotes if significantly lower than the data of PuraStat ® control (if $p < 0.05$, two tailed Student's t-test).

TABLE 8

HPLC test for major peptide contents of PuraStat ® (RADA16 (SEQ ID NO: 1) 2.5%) before and after X-ray and e-beam irradiation (N = 3, mean ± SD).

| Testing conditions | Major peptide content (%) |
|---|---|
| PuraStat ® control | 78.3 ± 1.7 |
| PuraStat ® irradiated (X-ray) at 25 kGy | 73.8 ± 1.7* |
| PuraStat ® irradiated (X-ray) at 40 kGy | 71.9 ± 0.8* |
| PuraStat ® irradiated (e-beam) at 25 kGy | 76.0 ± 0.9* |
| PuraStat ® irradiated (e-beam) at 40 kGy | 70.0 ± 2.4* |

*denotes if significantly lower than the data of PuraStat ® control (if $p < 0.05$, two tailed Student's t-test).

TABLE 9

HPLC test for major peptide contents of IEIK13 (SEQ ID NO: 3) 1.3% before and after gamma, X-ray, and e-beam irradiation (N = 3, t mean ± SD).

| Testing conditions | Major peptide content (%) |
|---|---|
| IEIK13 (SEQ ID NO: 3) control | 99.6 ± 0.0 |
| IEIK13 (SEQ ID NO: 3) irradiated (gamma) at 40 kGy | 99.8 ± 0.2 |

TABLE 9-continued

HPLC test for major peptide contents of IEIK13 (SEQ ID NO: 3) 1.3% before and after gamma, X-ray, and e-beam irradiation (N = 3, t mean ± SD).

| Testing conditions | Major peptide content (%) |
|---|---|
| IEIK13 (SEQ ID NO: 3) irradiated (X-ray) at 25 kGy | 99.8 ± 0.1 |
| IEIK13 (SEQ ID NO: 3) irradiated (X-ray) at 40 kGy | 99.9 ± 0.1 |
| IEIK13 (SEQ ID NO: 3) irradiated (e-beam) at 25 kGy | 99.6 ± 0.2 |
| IEIK13 (SEQ ID NO: 3) irradiated (e-beam) at 40 kGy | 99.8 ± 0.1 |

TABLE 10

HPLC test for major peptide contents of QLEL12 (SEQ ID NO: 4) 0.15% before and after gamma, X-ray, and e-beam irradiation (N = 3, mean ± SD).

| Testing conditions | Major peptide content (%) |
|---|---|
| QLEL12 (SEQ ID NO: 4) control | 90.5 ± 1.3 |
| QLEL12 (SEQ ID NO: 4) irradiated (gamma) at 40 kGy | 40.7 ± 3.1* |
| QLEL12 (SEQ ID NO: 4) irradiated (X-ray) at 25 kGy | 57.0 ± 4.9* |
| QLEL12 (SEQ ID NO: 4) irradiated (X-ray) at 40 kGy | 47.3 ± 1.3* |
| QLEL12 (SEQ ID NO: 4) irradiated (e-beam) at 25 kGy | 51.9 ± 7.3* |
| QLEL12 (SEQ ID NO: 4) irradiated (e-beam) at 40 kGy | 55.6 ± 3.0* |

*denotes if significantly lower than the data of QLEL12 (SEQ ID NO: 4) control (if $p < 0.05$, two tailed Student's t-test).

The major peptide content of RADA16 (SEQ ID NO:1) control was 78.3%. The major peptide contents of RADA16 (SEQ ID NO:1) after gamma irradiation at 23, 25, 28 and 40 kGy were 75.5, 74.6, 68.5 and 69.7%, respectively. The major peptide contents of RADA16 (SEQ ID NO:1) after X-ray irradiation at 25 and 40 kGy were 73.8 and 71.9%, respectively. The major peptide contents of RADA16 (SEQ ID NO:1) after e-beam irradiation at 25 and 40 kGy were 76.0 and 70.0%, respectively.

The major peptide content of IEIK13 (SEQ ID NO:3) control was 99.6%. The major peptide content of IEIK13 (SEQ ID NO:3) after gamma irradiation at 40 kGy was 99.8%. The major peptide contents of IEIK13 (SEQ ID NO:3) after X-ray irradiation at 25 and 40 kGy were 99.8 and 99.9%, respectively. The major peptide contents of IEIK13 (SEQ ID NO:3) after e-beam irradiation at 25 and 40 kGy were 99.6 and 99.8%, respectively.

The major peptide content of QLEL12 (SEQ ID NO:4) control was 90.5%. However, QLEL12 (SEQ ID NO:4) showed significant decrease in its major peptide content after irradiation sterilization. The major peptide content of QLEL12 (SEQ ID NO:4) after gamma irradiation at 40 kGy was 40.7%. The major peptide contents of QLEL12 (SEQ ID NO:4) after X-ray irradiation at 25 and 40 kGy were 57.0 and 47.3%, respectively. The major peptide contents of QLEL12 (SEQ ID NO:4) after e-beam irradiation at 25 and 40 kGy were 51.9 and 55.6%, respectively. These results demonstrate that RADA16 (SEQ ID NO:1) and IEIK13 (SEQ ID NO:3) remain relatively unchanged after gamma, X-ray and e-beam irradiation compared to QLEL12 (SEQ ID NO:4).

Figure 2A:
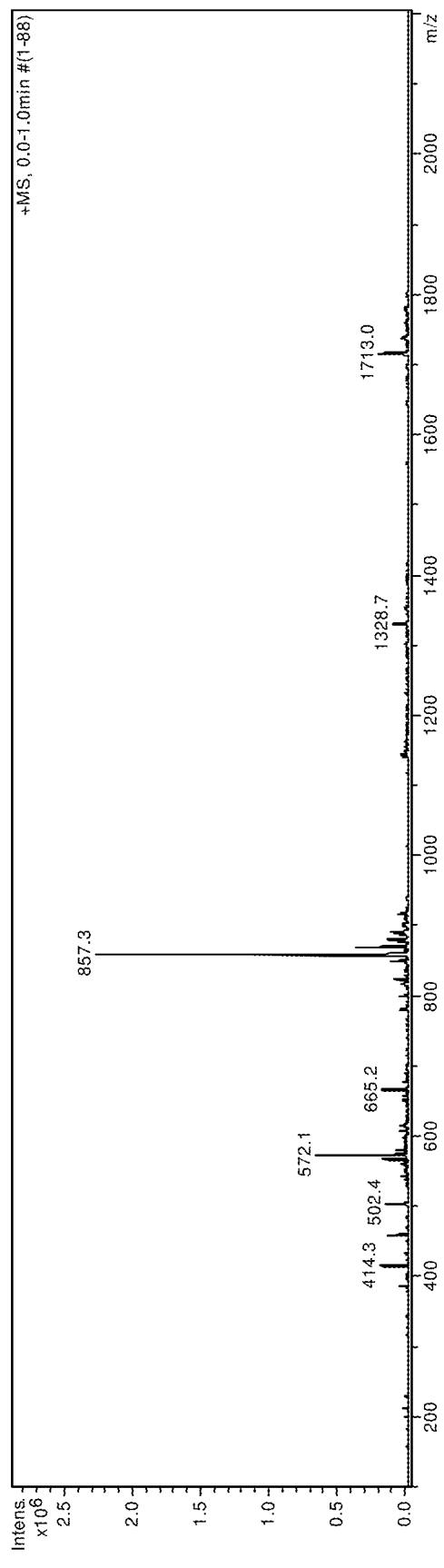
FIG. 2A shows the mass spectrum of PuraStat® (RADA16 (SEQ ID NO:1) 2.5%) before gamma irradiation.
Figure 2B:
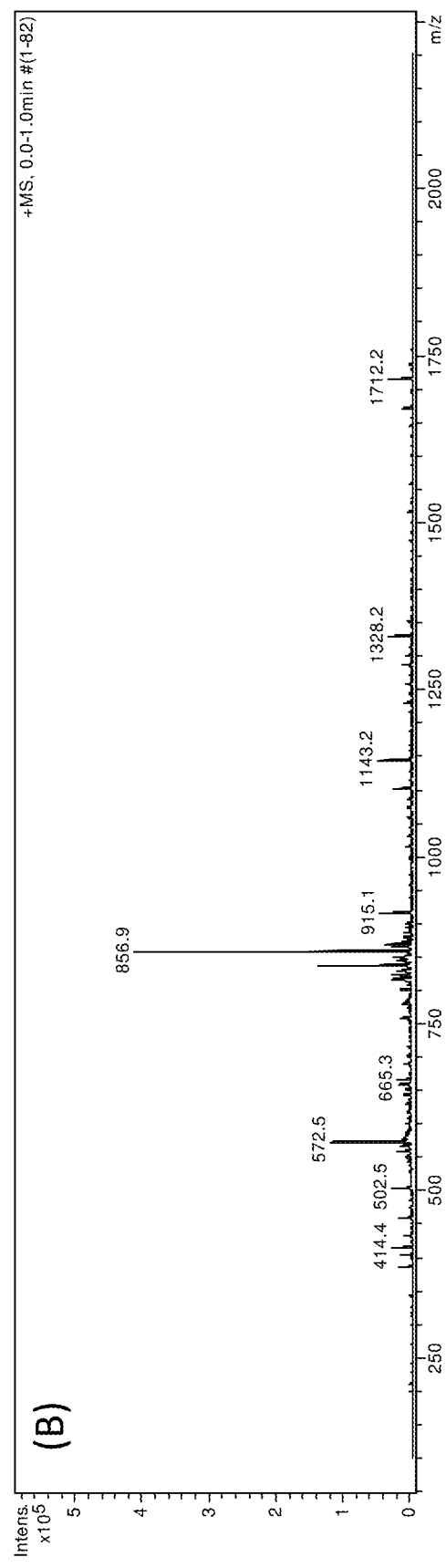
FIG. 2B shows the mass spectrum of PuraStat® (RADA16 (SEQ ID NO:1) 2.5%) after gamma irradiation at 40 kGy.
Figure 2C:
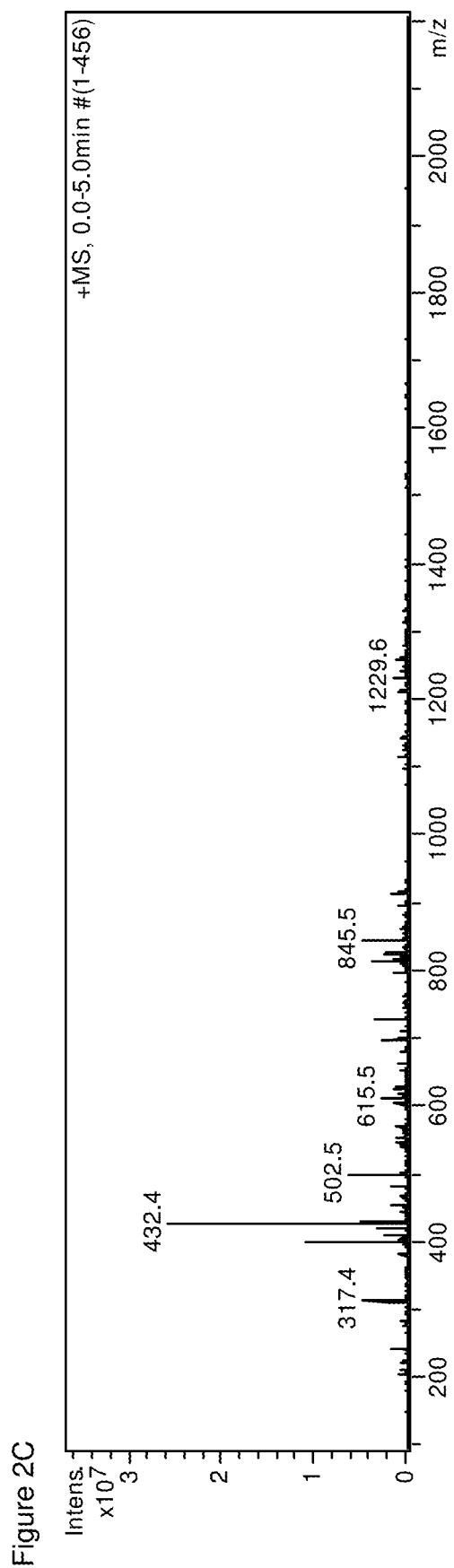
FIG. 2C shows the mass spectrum of PuraStat® (RADA16 (SEQ ID NO:1) 2.5%) after autoclaving at 121° C. for 20 min.
Figure 3A:
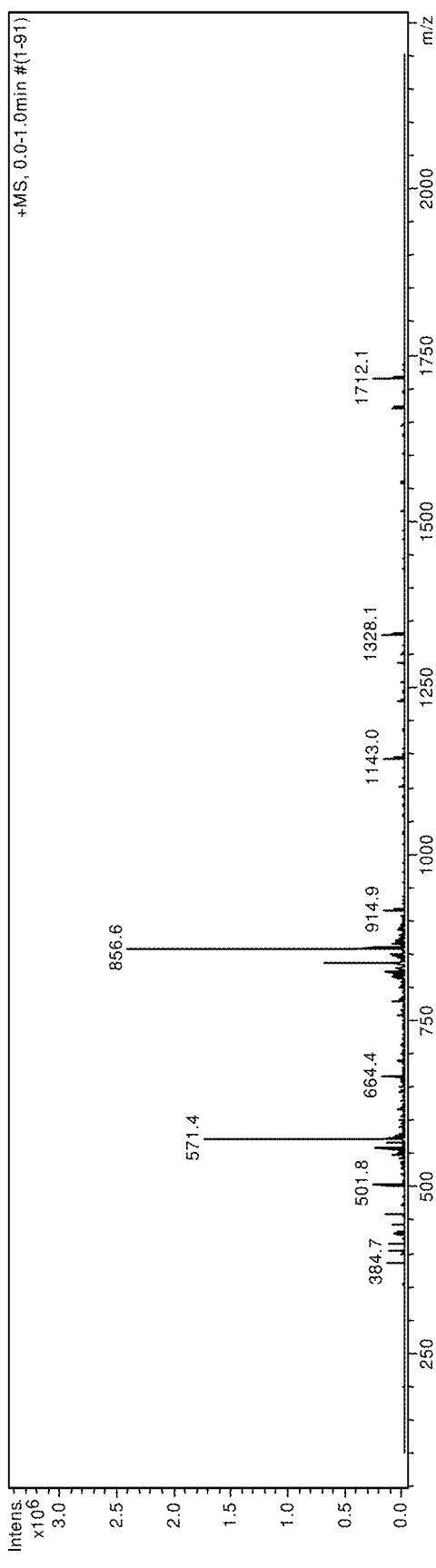
FIG. 3A shows the mass spectrum of PuraStat® (RADA16 (SEQ ID NO:1) 2.5%) after X-ray irradiation at 25 kGy.
Figure 3B:
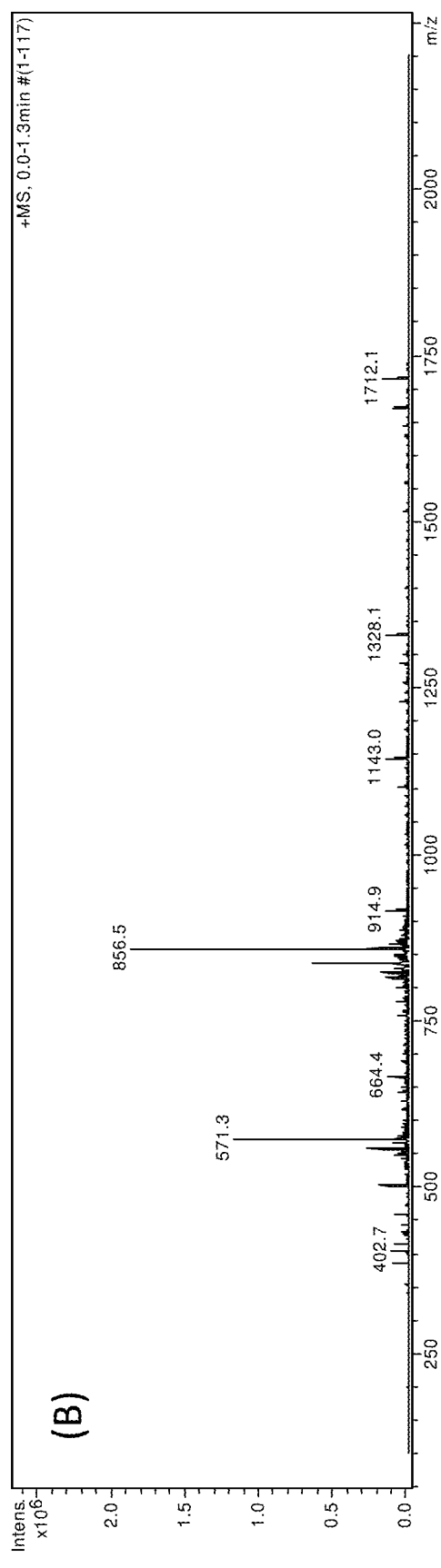
FIG. 3B shows the mass spectrum of PuraStat® (RADA16 (SEQ ID NO:1) 2.5%) after X-ray irradiation at 40 kGy.
Figure 4A:
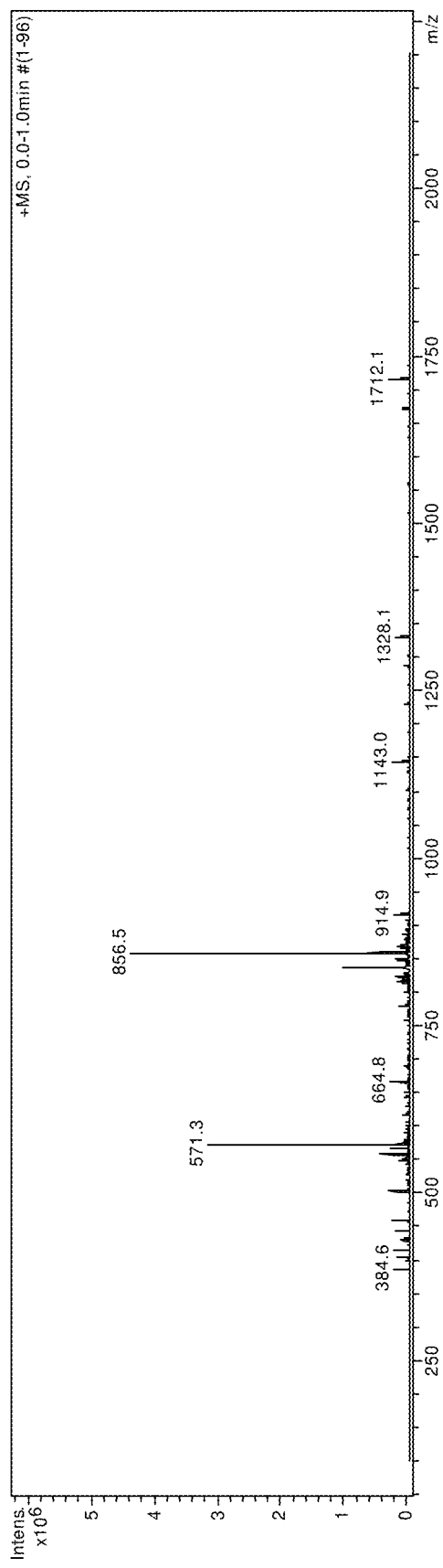
FIG. 4A shows the mass spectrum of PuraStat® (RADA16 (SEQ ID NO:1) 2.5%) after e-beam irradiation at 25 kGy.
Figure 4B:
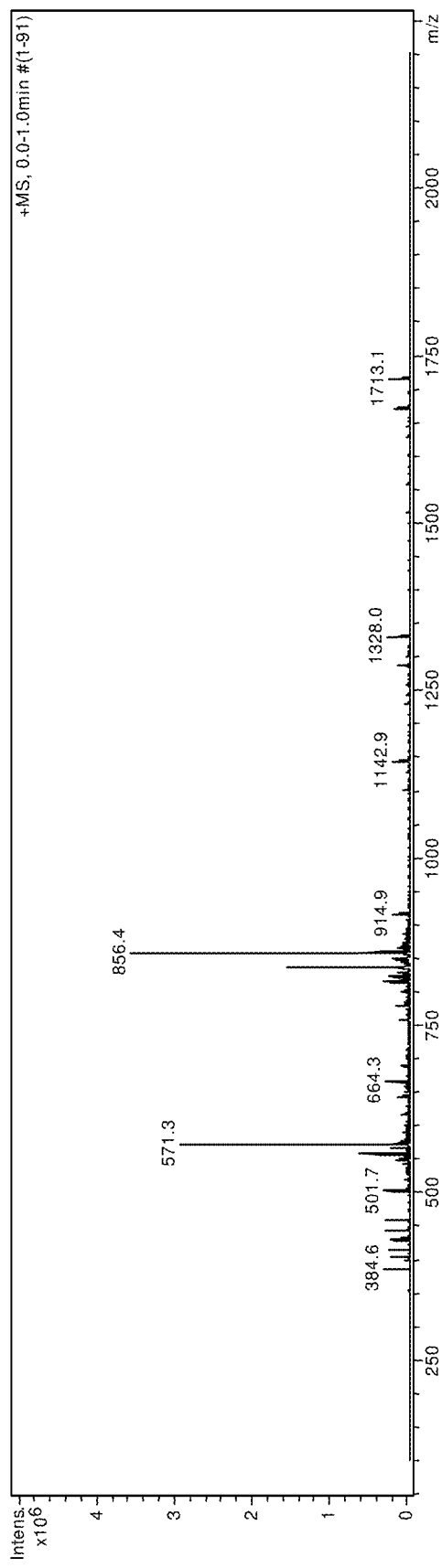
FIG. 4B shows the mass spectrum of PuraStat® (RADA16 (SEQ ID NO:1) 2.5%) after e-beam irradiation at 40 kGy.
Figure 5A:
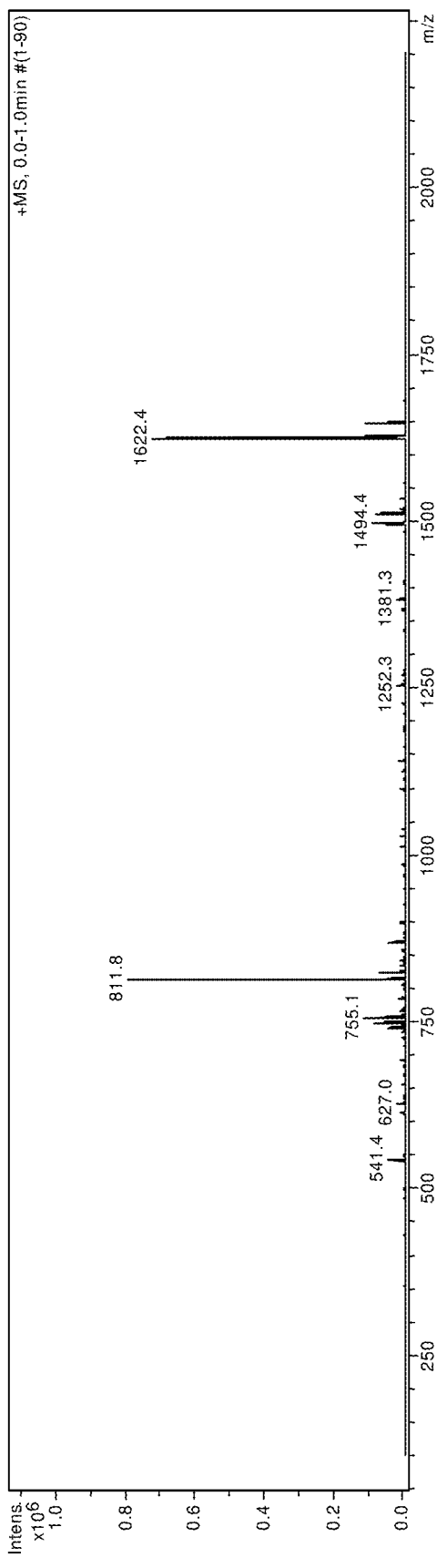
FIG. 5A shows the mass spectrum of IEIK13 (SEQ ID NO:3) 1.3% before irradiation.
Figure 5B:
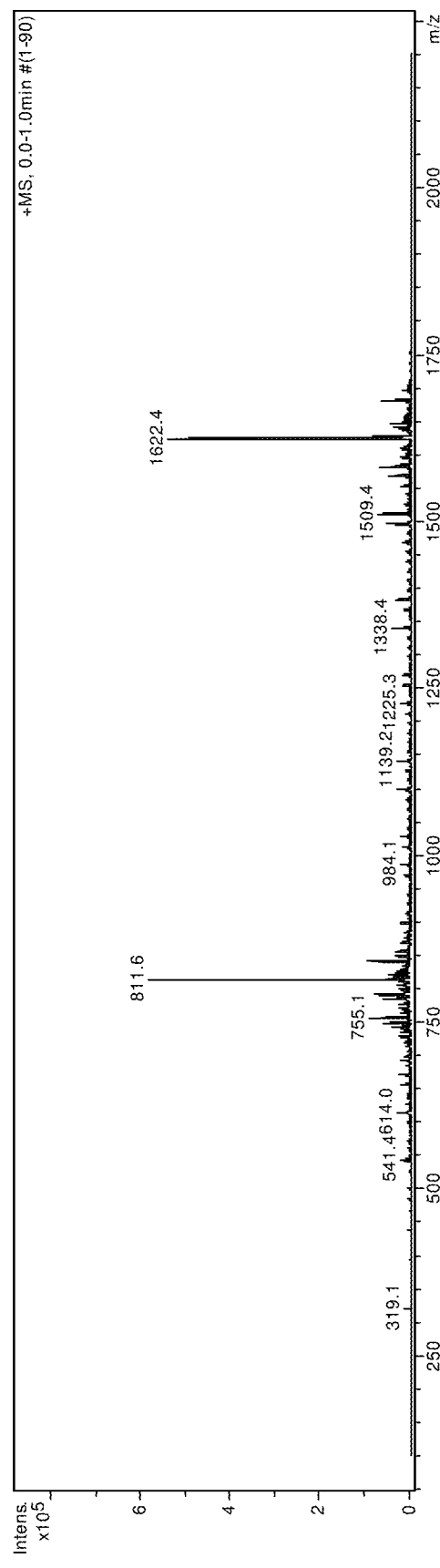
FIG. 5B shows the mass spectrum of IEIK13 (SEQ ID NO:3) 1.3% after gamma irradiation at 40 kGy.
Figure 5C:
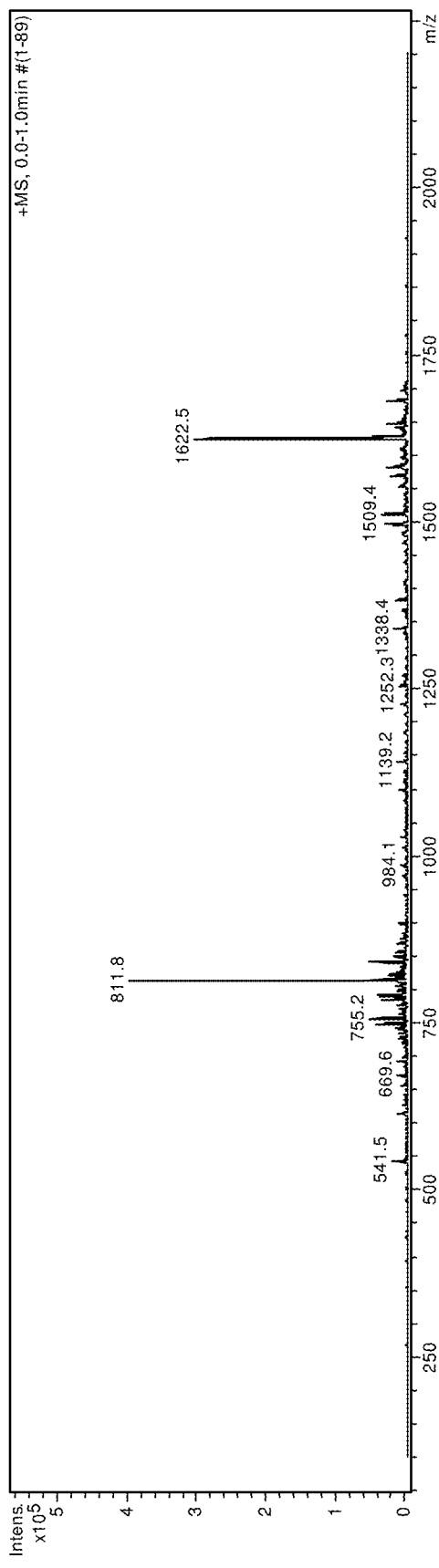
FIG. 5C shows the mass spectrum of IEIK13 (SEQ ID NO:3) 1.3% after X-ray irradiation at 25 kGy.
Figure 5D:
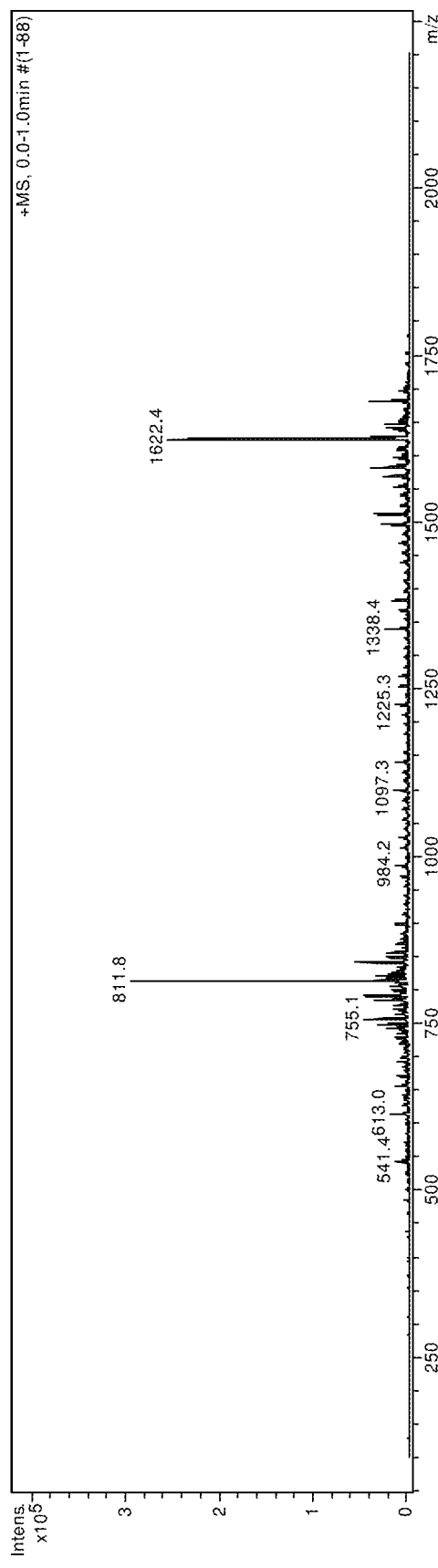
FIG. 5D shows the mass spectrum of IEIK13 (SEQ ID NO:3) 1.3% after X-ray irradiation at 40 kGy.
Figure 5E:
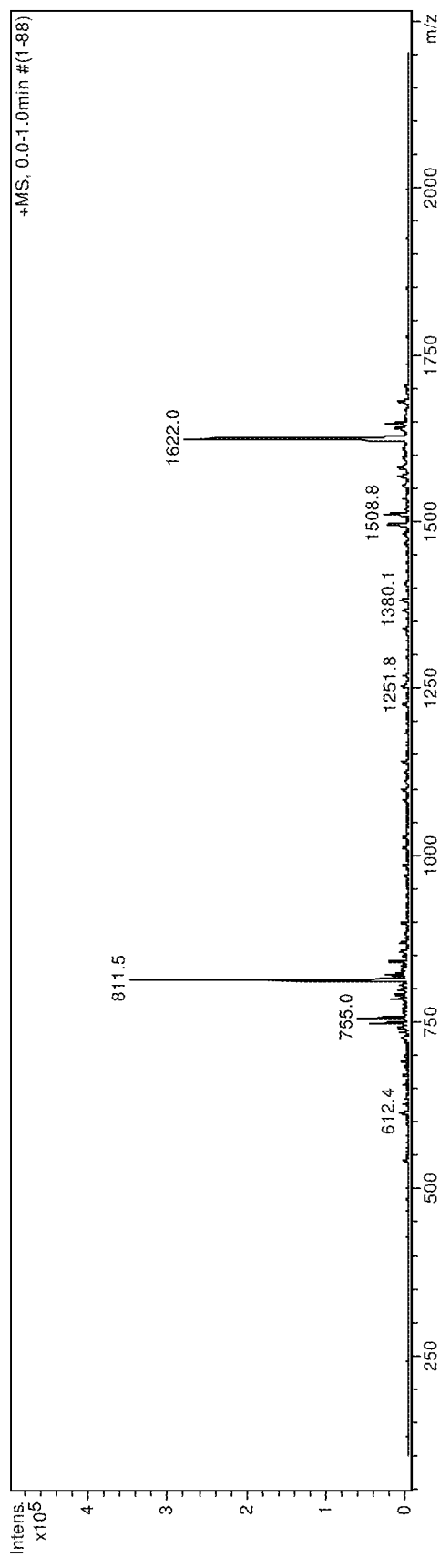
FIG. 5E shows the mass spectrum of IEIK13 (SEQ ID NO:3) 1.3% after e-beam irradiation at 25 kGy.
Figure 5F:
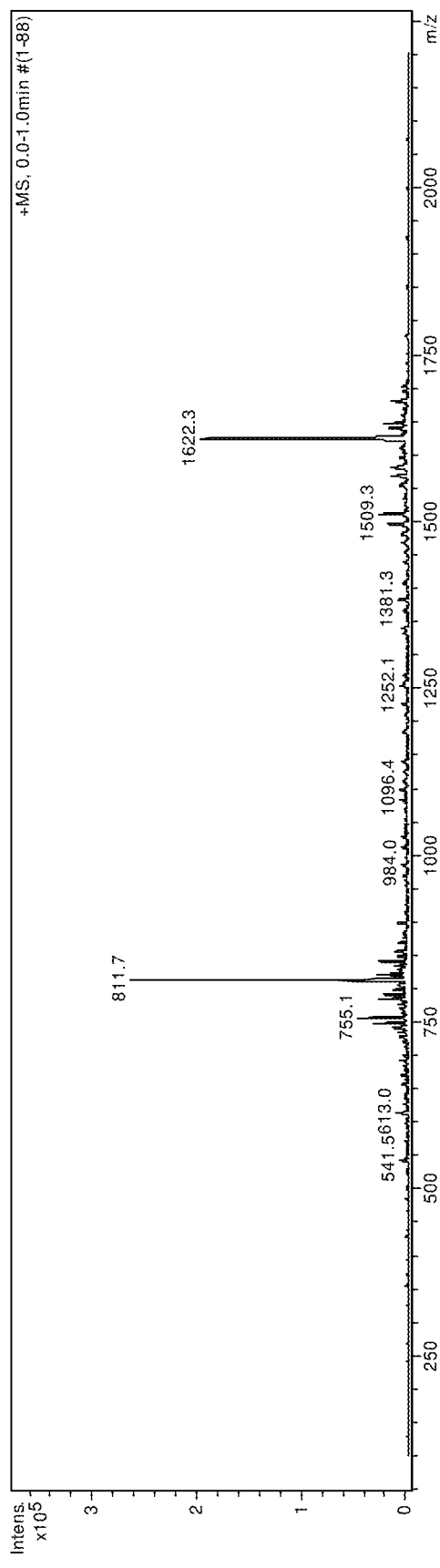
FIG. 5F shows the mass spectrum of IEIK13 (SEQ ID NO:3) 1.3% after e-beam irradiation at 40 kGy.
Figure 6A:
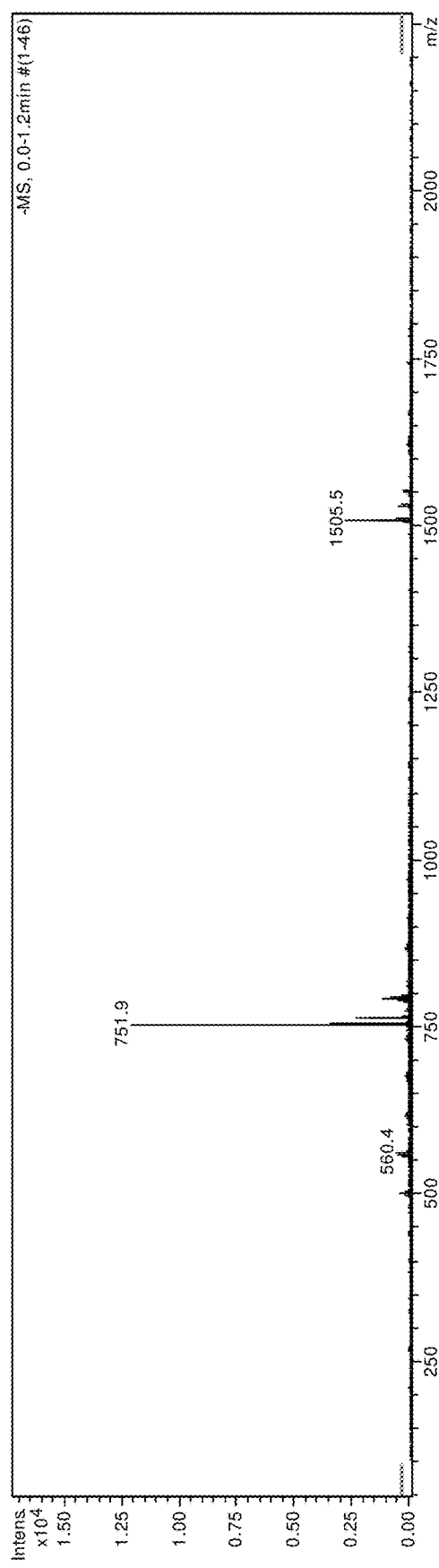
FIG. 6A shows the mass spectrum of QLEL12 (SEQ ID NO:4) 0.15% before irradiation.
Figure 6B:
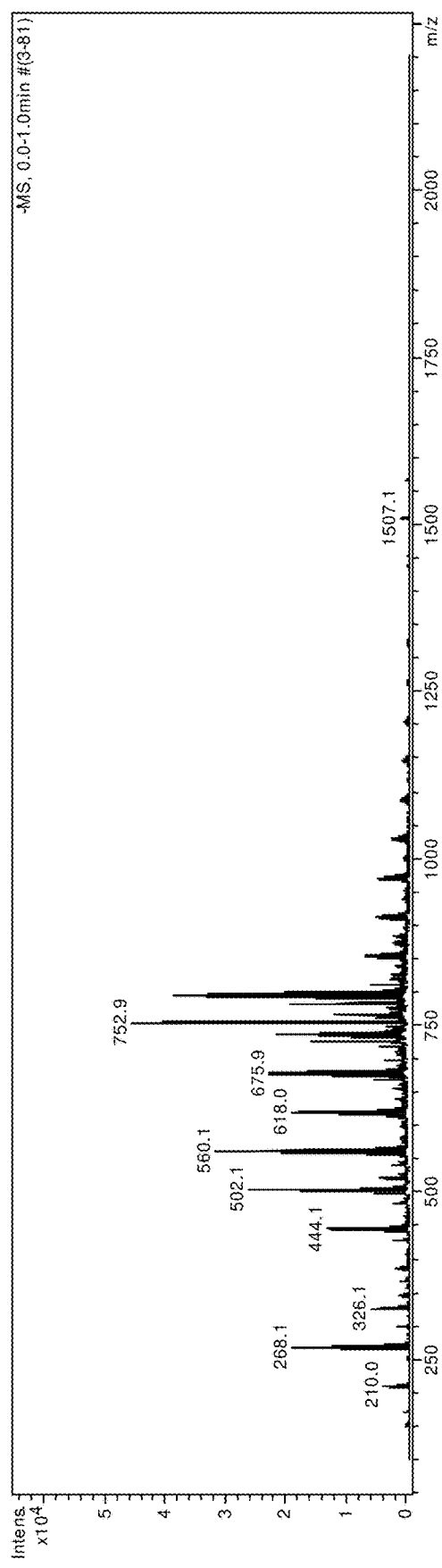
FIG. 6B shows the mass spectrum of QLEL12 (SEQ ID NO:4) 0.15% after gamma irradiation at 23 kGy.
Figure 6C:
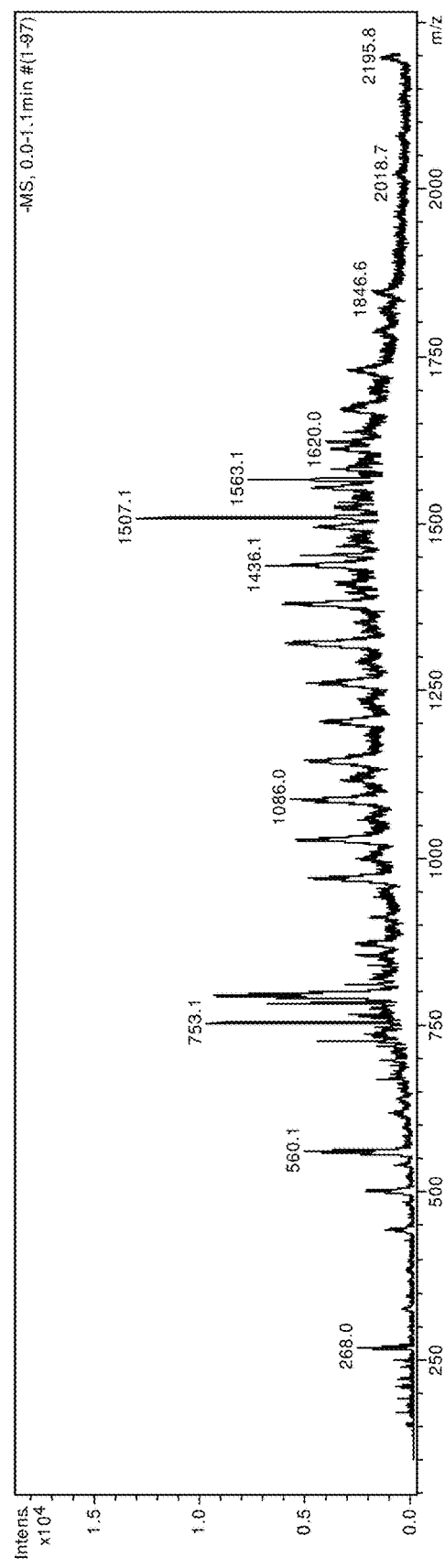
FIG. 6C shows the mass spectrum of QLEL12 (SEQ ID NO:4) 0.15% after X-ray irradiation at 25 kGy.
Figure 6D:
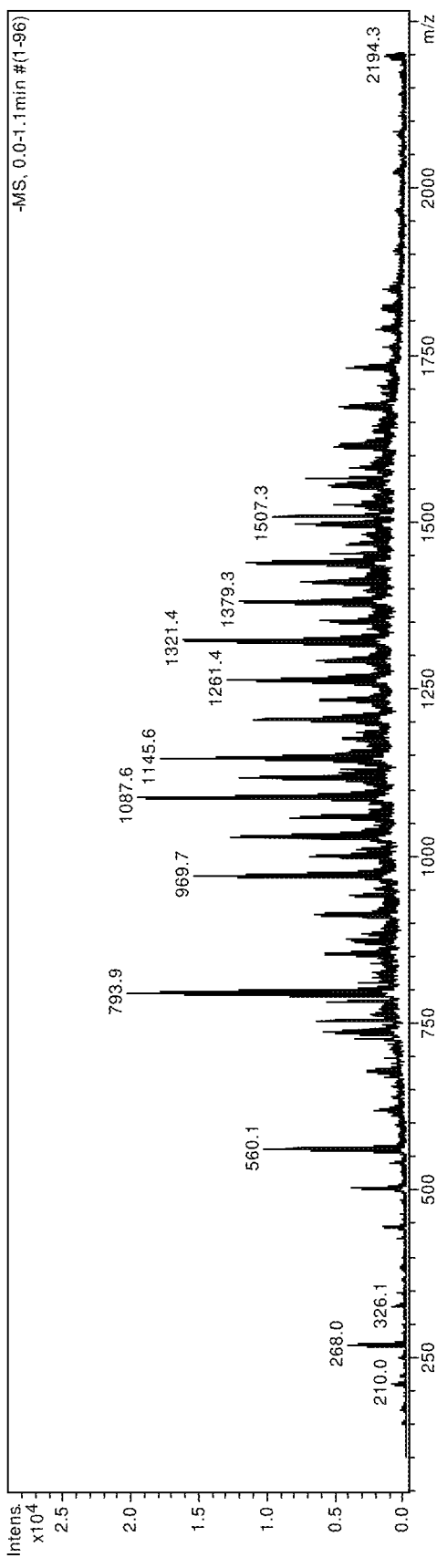
FIG. 6D shows the mass spectrum of QLEL12 (SEQ ID NO:4) 0.15% after X-ray irradiation at 40 kGy.
Figure 6E:
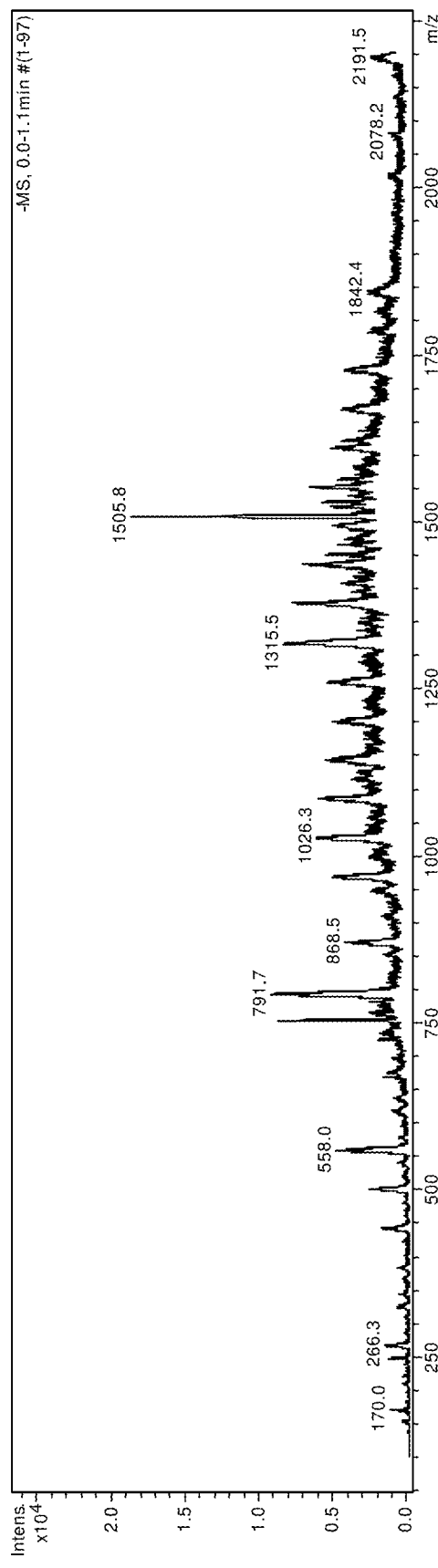
FIG. 6E shows the mass spectrum of QLEL12 (SEQ ID NO:4) 0.15% after e-beam irradiation at 25 kGy.
Figure 6F:
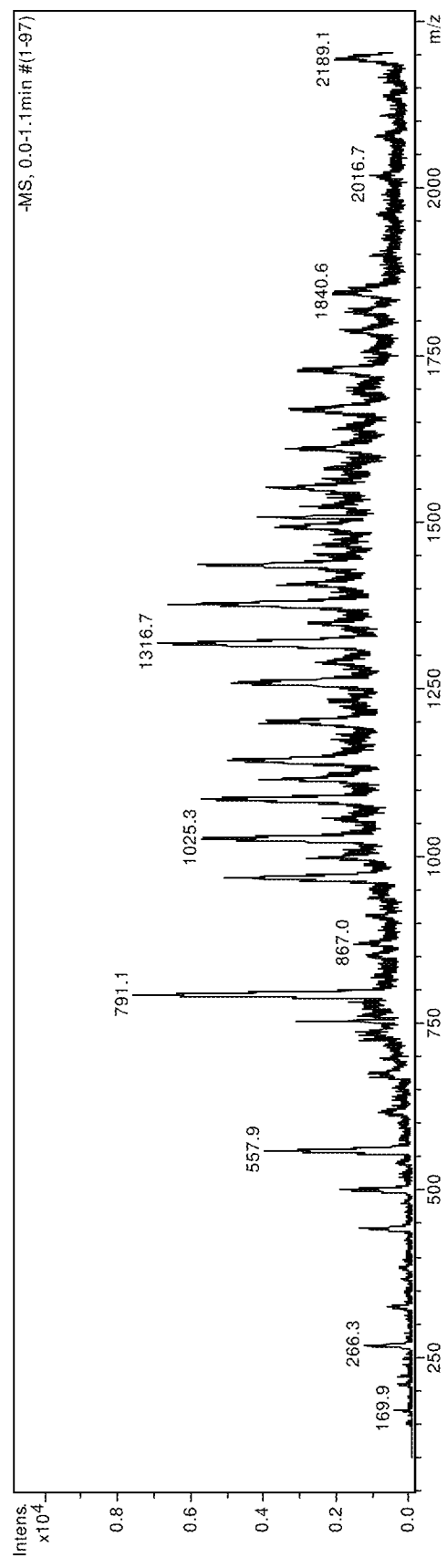
FIG. 6F shows the mass spectrum of QLEL12 (SEQ ID NO:4) 0.15% after e-beam irradiation at 40 kGy.

The measured molecular weight of RADA16 (SEQ ID NO:1) was 1712, which matches its calculated molecular weight (FIG. 2). The mass spectrometry analysis demonstrated that RADA16 (SEQ ID NO:1) was not degraded after gamma, X-ray or e-beam irradiation (FIGS. 2-4). However, RADA16 (SEQ ID NO:1) completely degraded during autoclave treatment.

Irradiation is a cold temperature sterilization technique unlike autoclaving. Although both sterilization techniques provide high energy (i.e., radiation and heat) to self-assembling peptides such as RADA16 (SEQ ID NO:1) during sterilization, irradiation sterilization did not induce substantial degradation of RADA16 (SEQ ID NO:1) molecules.

However, all gamma, X-ray, and e-beam irradiated PuraStat® mass spectra exhibited some peaks that were not observed before irradiation, while no notable difference was observed among them. The summary of the mass spectra is listed in Table 11.

DARADA-NH$_2$ (SEQ ID NO:8), ARADARADARA (SEQ ID NO:10), Ac-RADARADARAD (SEQ ID NO:11), respectively.

Table 12 shows the pattern of degradation of Ac-(RADA)$_4$-NH$_2$ (SEQ ID NO:1) when PuraStat® is stored at 2-8° C. for about 4 years. From the pattern, we found that degradation mainly occurs at the points between ~RAD and A~.

On the other hand, the irradiated PuraStat® showed additional M$_z$ peaks at 836/1670, 1100, and 1513, which are estimated as (RADA)$_4$-NH$_2$ (SEQ ID NO:7), ADARADARADA-NH$_2$ (SEQ ID NO:9), and ADARADARADARADA-NH$_2$ (SEQ ID NO:12), respectively.

Table 13 shows the additional pattern of degradation of Ac-(RADA)$_4$-NH$_2$ (SEQ ID NO:1) when PuraStat® is sterilized with irradiation. Especially, the peaks at 836 and 1670 are ones of major additional peaks, which represent RADARADARADARADA-NH$_2$ (SEQ ID NO:7). This

TABLE 11

Mass-spectrometry data of PuraStat ® after irradiation sterilization process.

| Mz | Mw at n = 1 | Mw at n = 2 | Mw at n = 3 | Estimated component | Control PuraStat ®* | Irradiated PuraStat ®* |
|---|---|---|---|---|---|---|
| 502 | 501 | | | ARADA-NH$_2$ (SEQ ID NO: 5) | Yes | Yes |
| 572 | | | 1712 | Ac-(RADA)$_4$-NH$_2$ (SEQ ID NO: 1) | Yes | Yes |
| 665 | | 1328 | | ARADARADARADA-NH$_2$ (SEQ ID NO: 6) | Yes | Yes |
| 836 | | 1670 | | (RADA)$_4$-NH$_2$ (SEQ ID NO: 7) | No | Yes |
| 857 | | | 1712 | Ac-(RADA)$_4$-NH$_2$ (SEQ ID NO: 1) | Yes | Yes |
| 916 | 915 | | | ARADARADA-NH$_2$ (SEQ ID NO: 8) | Yes | Yes |
| 1100 | 1100 | | | ADARADARADA-NH$_2$ (SEQ ID NO: 9) | No | Yes |
| 1143 | 1142 | | | ARADARADARA (SEQ ID NO: 10) | Yes | Yes |
| 1229 | 1228 | | | Ac-RADARADARAD (SEQ ID NO: 11) | Yes | Yes |
| 1329 | 1328 | | | ARADARADARADA-NH$_2$ (SEQ ID NO: 6) | Yes | Yes |
| 1513 | 1513 | | | ADARADARADARADA-NH$_2$ (SEQ ID NO: 12) | No | Yes |
| 1643 | 1642 | | | Ac-RADARADARADARAD (SEQ ID NO: 13) | Yes | Yes |
| 1670 | 1670 | | | (RADA)$_4$-NH$_2$ (SEQ ID NO: 7) | No | Yes |
| 1713 | 1712 | | | Ac-(RADA)$_4$-NH$_2$ (SEQ ID NO: 1) | Yes | Yes |

*: stored at 2-8° C. for about 4 years.
*: all PuraStat ® samples ware irradiated at 40 kGy (with gamma rays, X-rays, and e-beam)

The control PuraStat® showed M$_z$ peaks at 572, 857, and 1713, which are assigned to the major peptide, Ac-(RADA)$_4$-NH$_2$ (SEQ ID NO:1). Control PuraStat® also exhibited other peaks at 502, 665/1329, 916, 1143, and 1229 M$_z$, which are estimated as ARADA-NH$_2$ (SEQ ID NO:5), ARADARADARADA-NH$_2$ (SEQ ID NO:6), ARAmeans that irradiation can cause additional degradation of PuraStat® at the point between acetyl group (Ac) and RAD~. The peaks at 1100 and 1513 are also ones of major additional peaks, which represent ADARADARADA-NH$_2$ (SEQ ID NO:9), and ADARADARADARADA-NH$_2$ (SEQ ID NO:12). This means that irradiation can cause additional degradation of PuraStat® at the point between ~R and AD~.

TABLE 12

Pattern of degradation of Ac-(RADA)₄-NH₂ (SEQ ID NO: 1)
(PuraStat ® was stored at 2-8° C. for about 4 years)

Ac-RADARADARADARADA-NH₂ (SEQ ID NO: 1) (before degradation)

Ac-RAD/ARADARADARADA-NH₂ (SEQ ID NO: 6)

Ac-RADARAD (SEQ ID NO: 14)/ARADARADA-NH₂ (SEQ ID NO: 8)

Ac-RADARADARAD (SEQ ID NO: 11)/ARADA-NH₂ (SEQ ID NO: 5)

Ac-RAD/ARADARADARA (SEQ ID NO: 10)/DA-NH₂

Ac-RADARADARADARAD (SEQ ID NO: 13)/A-NH₂

TABLE 13

Additional pattern of degradation of Ac-(RADA)₄-NH₂ (SEQ ID
NO: 1) when PuraStat ® is sterilized with irradiation Ac-RADARADARADARADA-NH₂ (SEQ ID NO: 1) (before degradation)

Ac/RADARADARADARADA-NH₂ (SE ID NO: 7)

Ac-R/ADARADARADARADA-NH₂ (SEQ ID NO: 12)

Ac-RADAR (SEQ ID NO: 15)/ADARADARADA-NH₂ (SEQ ID NO: 9)

Also, the molecular weight of IEIK13 (SEQ ID NO:3) was measured at 1622, which matches its calculated molecular weight (FIG. 5). The mass spec analysis demonstrated that IEIK13 (SEQ ID NO:3) was only insubstantially degraded after gamma-ray, X-ray, and e-beam irradiation.

Furthermore, the molar mass of QLEL12 (SEQ ID NO:4) was measured at 1506, which matches its calculated molar mass (FIG. 6). However, the mass spec analysis demonstrated that QLEL12 (SEQ ID NO:4) was significantly degraded after gamma-ray, X-ray, and e-beam irradiation.

Example 7: Rheological Properties

Based on ISO 11137 (Sterilization of health care products—Radiation), radiation sterilization methods can be used with 25 kGy or 15 kGy irradiation as the sterilization dose to achieve a sterility assurance level, SAL, of $10^{-6}$.

Figure 7:
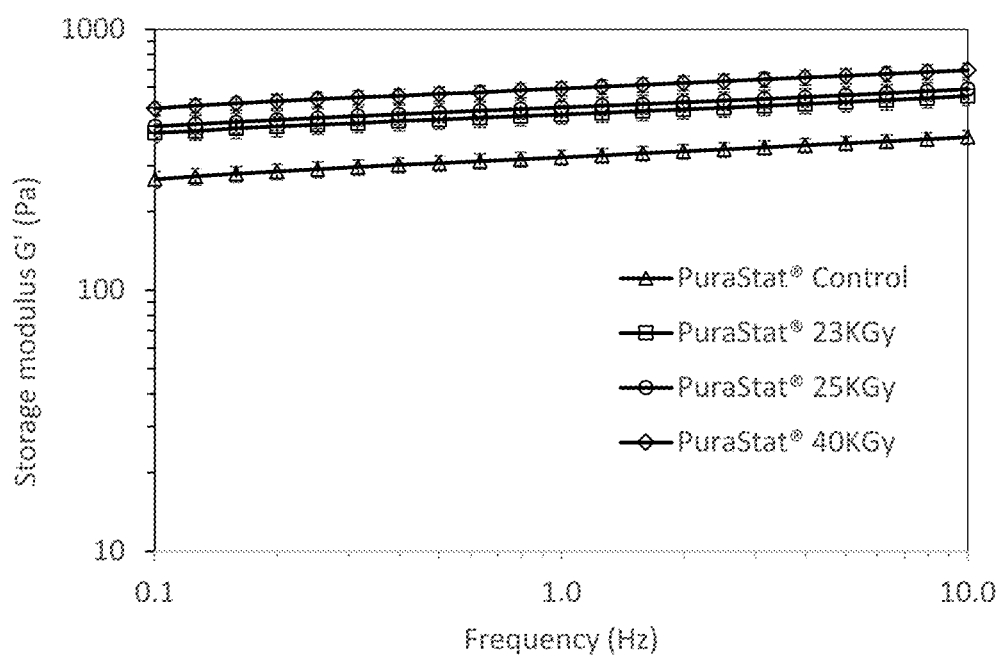
FIG. 7 shows results of a frequency test of PuraStat® (RADA16 (SEQ ID NO:1) 2.5%) with gamma irradiation at 0.1% of strain with 40 mm cone-plate (N=3, bars represent SD).
Figure 8:
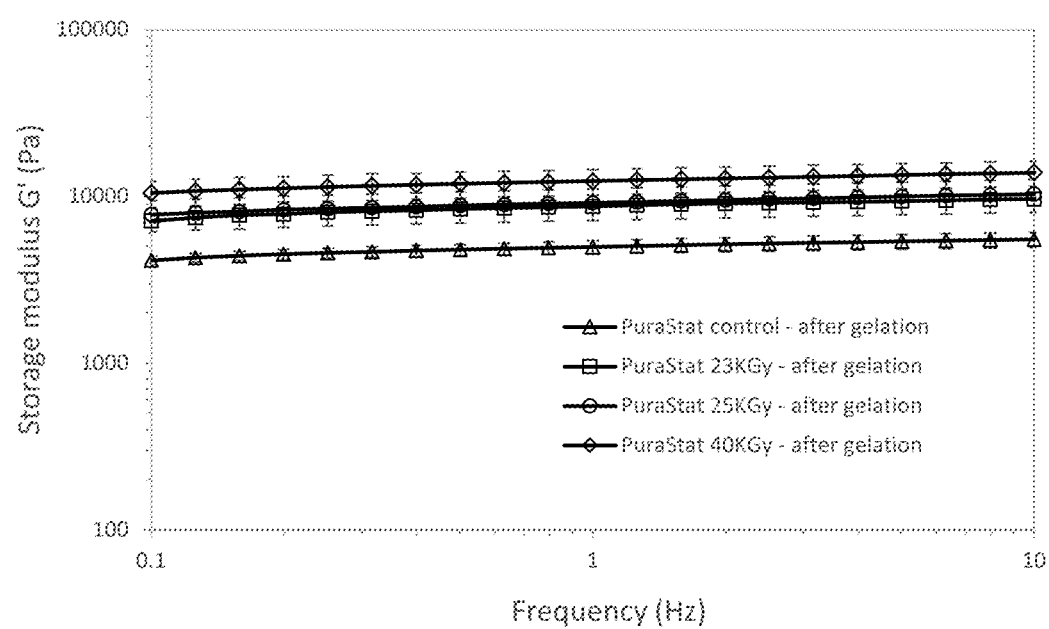
FIG. 8 shows results of a frequency test of PuraStat® (RADA16 (SEQ ID NO:1) 2.5%) with gamma irradiation after gelation at 0.1% of strain with 40 mm cone-plate. Samples were treated with DMEM for 20 min (N=3, bars represent SD).

The rheology results are shown in FIGS. 7 and 8 for PuraStat® with gamma irradiation sterilization before and after gelation, respectively. The determined rheological results are listed in Tables 14-15.

TABLE 14

Results from frequency tests of PuraStat ®
(RADA16 (SEQ ID NO: 1) 2.5%) with gamma irradiation
at 0.1% of strain with 40 mm cone-plate

| | Storage Modulus G' at 1 Hz (Pa) | | | |
|---|---|---|---|---|
| Sample # | PuraStat ® control | Gamma-irradiated PuraStat ® at 23 kGy | Gamma-irradiated PuraStat ® at 25 kGy | Gamma-irradiated PuraStat ® at 40 kGy |
| 1 | 343.7 | 514.1 | 546.0 | 551.0 |
| 2 | 323.3 | 449.7 | 490.2 | 607.7 |
| 3 | 301.7 | 449.5 | 467.0 | 618.4 |
| Mean | 322.9 | 471.1* | 501.0* | 592.4*,$ |
| SD | 21.0 | 37.2 | 40.6 | 36.2 |

*denotes if p < 0.05 compared to control (two tailed Student's t-test).
$denotes if p < 0.05 compared to the others (two tailed Student's t-test).

PuraStat® gamma-irradiated at 23 kGy, 25 kGy, and 40 kGy showed higher storage modulus than PuraStat® control (FIG. 7 and Table 14). PuraStat® gamma-irradiated at 40 kGy showed significantly higher storage modulus than PuraState® gamma-irradiated at 23 and 25 kGy. Also, PuraStat® gamma-irradiated at 25 kGy showed slightly higher storage modulus than PuraStat® gamma-irradiated at 23 kGy.

This indicates that gamma-irradiation positively affected the rheological properties of PuraStat®. PuraStat® gamma-irradiated at 23 kGy (471.1±37.2 Pa), 25 kGy (501.0±40.6 Pa) and 40 kGy (592.4±36.2 Pa) exhibited 46%, 55%, and 83% increases in their storage moduli, respectively, compared to PuraStat® control (322.9±21.0 Pa).

TABLE 15

Results from frequency tests of PuraStat ® (RADA16
(SEQ ID NO: 1) 2.5%) with gamma irradiation after
gelation. Samples were treated with DMEM for 20
min at 0.1% of strain with a 40 mm cone-plate

| | Storage Modulus G' at 1 Hz (Pa) | | | |
|---|---|---|---|---|
| Sample # | PuraStat ® control | Gamma-irradiated PuraStat ® at 23 kGy | Gamma-irradiated PuraStat ® at 25 kGy | Gamma-irradiated PuraStat ® at 40 kGy |
| 1 | 4454 | 8866 | 6885 | 14568 |
| 2 | 5280 | 8845 | 10395 | 10286 |
| 3 | 5183 | 8622 | 10148 | 12134 |
| Mean | 4972 | 8711* | 9143* | 12330* |
| SD | 451 | 135 | 1959 | 2148 |

*denotes if p < 0.05 compared to control (two tailed Student's t-test).
$ denotes if p < 0.05 compared to the others (two tailed Student's t-test).

Furthermore, after gelation triggered by simulated body fluid (i.e., DMEM buffer) for 20 min, PuraStat® gamma-irradiated at 23 kGy (8711±135 Pa), 25 kGy (9143±1959 Pa) and 40 kGy (12330±2148 Pa) exhibited 75%, 84%, and 148% increases in their storage moduli, respectively, compared to PuraStat® control (4972±451 Pa) (FIG. 8 and Table 11).

The rheology results are shown in Tables 16 and 17 for PuraStat® with X-ray irradiation sterilization before and after gelation, respectively.

TABLE 16

Results from frequency tests of PuraStat®
(RADA16 (SEQ ID NO: 1) 2.5%) with X-ray irradiation
at 0.1% of strain with 40 mm cone-plate

| | Storage Modulus G' at 1 Hz (Pa) | | |
|---|---|---|---|
| Sample # | PuraStat® control | X-ray-irradiated PuraStat® at 25 kGy | X-ray-irradiated PuraStat® at 40 kGy |
| 1 | 343.7 | 448.3 | 610.2 |
| 2 | 323.3 | 429.3 | 632.5 |
| 3 | 301.7 | 471.7 | 578.9 |
| Mean | 322.9 | 449.8* | 607.2*,$ |
| SD | 21.0 | 21.2 | 27.0 |

*denotes if p < 0.05 compared to control (two tailed Student's t-test).
$denoted if p < 0.05 compared to the others (two tailed Student's t-test).

PuraStat® X-ray-irradiated at 25 kGy and 40 kGy also showed higher storage modulus than PuraStat® control. PuraStat® X-ray-irradiated at 40 kGy showed significantly higher storage modulus that PuraStat® X-ray-irradiated at 25 kGy. This indicates X-ray irradiation positively affected the rheological properties of PuraStat®. PuraStat® irradiated at 25 kGy (449.8±21.2) and 40 kGy (607.2±27.0 Pa) exhibited 39% and 88% increases in their storage moduli, respectively, compared to PuraStat® control (322.9±21.0 Pa) (Table 17).

TABLE 17

Results from frequency tests of PuraStat® (RADA16
(SEQ ID NO: 1) 2.5%) with X-ray irradiation after
gelation. Samples were treated with DMEM for 20
min at 0.1% of strain with a 40 mm cone-plate.

| | Storage Modulus G' at 1 Hz (Pa) | | |
|---|---|---|---|
| Sample # | PuraStat® control | X-ray-irradiated PuraStat® at 25 kGy | X-ray-irradiated PuraStat® at 40 kGy |
| 1 | 4454 | 9563 | 12832 |
| 2 | 5280 | 6404 | 10611 |
| 3 | 5183 | 9522 | 10294 |
| Average | 4972 | 8497* | 11246* |
| SD | 451 | 1812 | 1383 |

*denotes if p < 0.05 compared to control (two tailed Student's t-test).

Furthermore, after gelation triggered by simulated body fluid (i.e., DMEM buffer) for 20 min, PuraStat® X-ray-irradiated at 25 kGy (8497±1812 Pa) and 40 kGy (11246±1383 Pa) exhibited 71% and 126% increases in their storage moduli, respectively, compared to PuraStat® control (4972±451 Pa) (Table 17).

The rheology results are shown in Tables 18 and 19 for PuraStat® with e-beam irradiation sterilization before and after gelation, respectively.

TABLE 18

Results from frequency tests of PuraStat®
(RADA16 (SEQ ID NO: 1) 2.5%) with e-beam irradiation
at 0.1% of strain with 40 mm cone-plate.

| | Storage Modulus G' at 1 Hz (Pa) | | |
|---|---|---|---|
| Sample # | PuraStat® control | e-beam-irradiated PuraStat® at 25 kGy | e-beam-irradiated PuraStat® at 40 kGy |
| 1 | 343.7 | 348.1 | 349.6 |
| 2 | 323.3 | 356.1 | 371.5 |

TABLE 18-continued

Results from frequency tests of PuraStat®
(RADA16 (SEQ ID NO: 1) 2.5%) with e-beam irradiation
at 0.1% of strain with 40 mm cone-plate.

| | Storage Modulus G' at 1 Hz (Pa) | | |
|---|---|---|---|
| Sample # | PuraStat® control | e-beam-irradiated PuraStat® at 25 kGy | e-beam-irradiated PuraStat® at 40 kGy |
| 3 | 301.7 | 324.0 | 338.4 |
| Mean | 322.9 | 342.7 | 353.2 |
| SD | 21.0 | 16.7 | 16.8 |

PuraStat® e-beam-irradiated at 25 kGy and 40 kGy, however, did not show a significant change in storage modulus compared to PuraStat® control. This indicates e-beam irradiation sterilization does not have a major effect on the rheological properties of PuraStat®. However, although the p values did not show statistical significance (i.e., p>0.05), PuraStat® X-ray-irradiated at 25 kGy (342.7±16.7 Pa) and 40 kGy (353.2±16.8 Pa) exhibited 6% and 9% increases in their storage moduli, respectively, compared to PuraStat® control (322.9±21.0 Pa) (Table 18).

TABLE 19

Results from frequency tests of PuraStat® (RADA16
(SEQ ID NO: 1) 2.5%) with e-beam irradiation after
gelation. Samples were treated with DMEM for 20
min at 0.1% of strain with 40 mm cone-plate.

| | Storage Modulus G' at 1 Hz (Pa) | | |
|---|---|---|---|
| Sample # | PuraStat® control | e-beam-irradiated PuraStat® at 25 kGy | e-beam-irradiated PuraStat® at 40 kGy |
| 1 | 4454 | 3623 | 4918 |
| 2 | 5280 | 4830 | 9327 |
| 3 | 5183 | 3542 | 7875 |
| Average | 4972 | 4007 | 7373 |
| SD | 451 | 715 | 2247 |

After gelation triggered by simulated body fluid (i.e., DMEM buffer) for 20 min, PuraStat® e-beam-irradiated at 25 kGy and 40 kGy did not show significant difference (i.e., the p values were higher than 0.05) in their storage moduli compared to PuraStat® control (Table 19).

Figure 9:
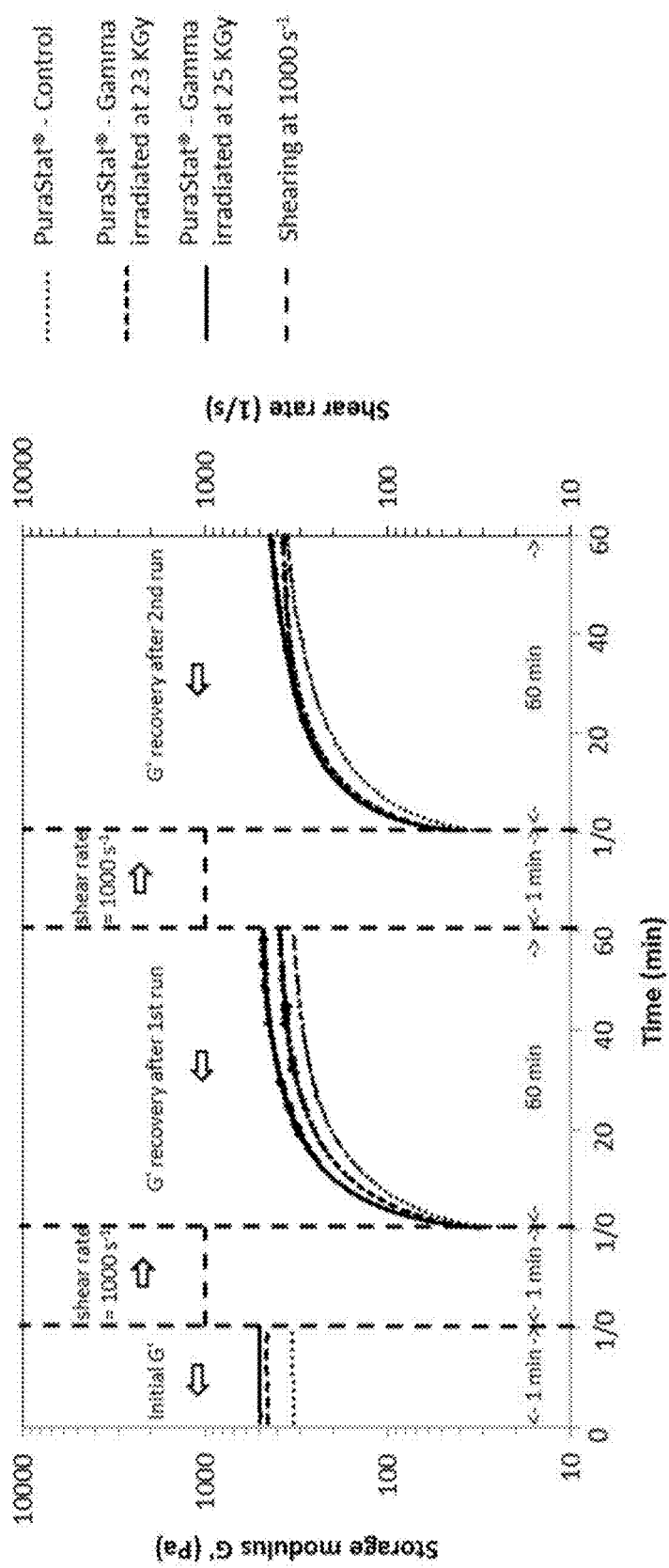
FIG. 9 shows results of a thixotropic test of PuraStat® (RADA16 (SEQ ID NO:1) 2.5%) with gamma irradiation at 1 Hz of frequency and 0.1% of strain with 40 mm cone-plate. Initial storage modulus (G') was measured for 1 min before 1st shearing at 1000 $s^{-1}$. After the 1st shearing for 1 minute, G' recovery was recorded for 1 hour to exhibit the thixotropic behavior of PuraStat®. This test was duplicated.

PuraStat® demonstrated shear thinning at high shear rate and thixotropic behavior suggesting slow rheological property recovery when high shearing stopped (FIG. 9). From these properties of PuraStat®, the stiffness of PuraStat® can be lowered for easier handling during application to patients and stiffness can then slowly recover to initial values after application. These intrinsic thixotropic properties of PuraStat® were not changed, even after gamma irradiation at 23 and 25 kGy, while irradiated PuraStat® showed higher storage modulus than PuraStat® control.

Because the peptides' molecular structure was not substantially changed considering the results of HPLC and Mass Spectrometry, the assembled nanofibrous structure of the peptides could be a factor to increase their rheological properties. The rheological properties of self-assembling peptide solution might increase when self-assembled peptide structure is more organized. By way of a non-binding theory, high energy from irradiation can make peptide molecules move slightly to have more organized nanofibrous structure resulting in improved rheological properties.

The increased rheological properties were at least partially reversed by repeated high shearing and returned back close to the original levels. After thoroughly shearing them twice at 1000 s$^{-1}$ for 1 minute, PuraStat® samples irradiated at 23 kGy and 25 kGy showed gradual decrease in their storage modulus from 484.5 Pa to 410.9 Pa and 514.3 Pa to 426.5 Pa, respectively, while PuraStat® control did not show significant change in its storage modulus (FIG. 9). It could be expected that the rheological properties of irradiated PuraStat® become closer to those of PuraStat® control with more shearing. Therefore, gamma irradiation enhances the structure of self-assembled nanofibers to increase their rheological properties without a detectable change in peptide molecular structure degradation or crosslinking.

Example 8: Bioburden Testing

A. Collection of Samples. Upon irradiation, 50 samples were collected as follows: 10 samples for bioburden tests inside the packages (collecting 4 at the beginning, each 3 at the middle and the end of the packaging operation); 10 samples for bioburden tests of the filling liquid in the syringe (collecting 4 at the beginning, each 3 at the middle and the end of the packaging operation); spare samples, e.g. 30 samples, may be collected in case extra testing may be required.

B. Viable Bacteria Count Test for Sterilization Validation. The sample was aseptically prepared in a clean bench, and all instruments and solvents to be used were sterilized.

For blister-packaged products, the following procedure was repeated twice with one sealed package to make a total 100 mL of sample solution. A syringe was used to inject 50 mL of rinsing fluid for the sterilization test (USP Fluid D) into the inside of the package. A sample were shaken thoroughly and allowed to stand to reduce bubbles. Then, the outside opening of the package was sterilized by lightly passing the opening through a flame without heating the contents. Then, a syringe or another suitable method was used to extract all the injected solution from the package, which was then collected in a heat-resistant bottle. With a sealed blister package containing about 100 CPU of spores purified from a standard strain such as *Bacillus subtilis* (NBRC3134), a recovery rate and a correction coefficient based on the recovery rate were calculated in advance from the viable bacteria count and the added bacteria count from a sample which was prepared in the same manner as above. A correction coefficient was calculated as 1/recovery rate (%)×100. This correction coefficient was recalculated when the sample preparation procedure was changed.

For testing content fluid, 1 mL of the content solution was mixed with 9 mL of Soybean-Casein Digest Medium agar medium (SCD agar medium), and the gel finely dispersed to make 10 mL of sample solution.

For blister package products, 100 mL of the sample solution per culture medium was used and the test was conducted using the membrane filter method of the Japanese Pharmacopoeia Microbial Limit Test.

For testing content fluid, 1 mL of the sample solution per culture medium and conduct the test using the agar plate dilution method of the Japanese Pharmacopoeia Microbial Limit Test. This test was repeated 10 times to obtain 10 culture media plates corresponding to 10 mL of sample solution.

The cultures were maintained at 30° C.-35° C. for 3-5 days (or longer) on SCD agar medium. As a general rule, the cultures were observed at least once every operating day during the culture period and on the final measurement day.

After completion of the culture, the actual measured values of the colonies of SCD agar medium were converted with the following calculation:
(1) For blister package products
 Viable bacteria count in a blister package=Viable bacteria count in 100 mL of sample liquid×Correction coefficient
(2) For Content fluid
 Viable bacteria count in 1 mL of content liquid=Total viable bacteria count in 10 mL equivalent to sample solution (10 culture media plates)

Remarks: Among the test method for the content fluid, the value of the SIP (aliquot) used for calculation were determined to be 1/5=0.2, not the total amount when testing with a 5-mL product by the test method equivalent to 1 mL of content liquid. *SIP (Sample Item Portion) is equivalent to an aliquot (defined portion of the healthcare product used for testing).

Example 9: Experimental Design of PuraStat® Sterilization by Gamma Irradiation

Irradiation conditions—PuraStat® samples (Lot #17C09A30) were irradiated with gamma rays at 25, 28 and 40 kGy with Gammacell 220® High Dose Rate Co-60 Irradiator (MDS Nordion, Ottawa, Canada). The run dose rate and duration time for 40 kGy irradiation were 6.30 kGy/hr and 6 hours 20 minutes 58 seconds, respectively. The run dose rate and duration time for 28 kGy irradiation were 4.40 kGy/hr and 6 hours 22 minutes 31 seconds, respectively. The run dose rate and duration time for 25 kGy irradiation were 6.58 kGy/hr and 3 hours 47 minutes 42 seconds, respectively.

Methods and test results: The appearance of PuraStat® was observed after each test. The pH of PuraStat® was tested using an Accumet AB15 pH meter (Fisher Scientific). HPLC tests were performed to evaluate the major peptide content after irradiation tests. Agilent HPLC 1100 (Agilent Technologies) was used for this study. Column temperature was kept at 25° C.

Solvent A was water with 0.1% TFA and solvent B was 80% Acetonitrile with 0.1% TFA. Gradient of solvent B was controlled from 10% to 40% in 20 min and 40% for another 5 min at 25° C. Agilent Zorbax 300SB-C18 column (4.6 mm×250 mm, 5 m, 300 Å) was used for this test. PuraStat® (RADA16 (SEQ ID NO:1) 2.5%) (40 mg) were mixed with 10 μL of DH$_2$O and 500 μL of formic acid and vortexed. And the mixture was mixed with DH$_2$O (4,450 μL) and vortexed. 20 μL of samples were injected using an Agilent autosampler.

Mass spectrometry tests were carried out to investigate the degradation of the peptides after irradiation sterilization. Agilent LC/MSD ion trap mass spectrometer was used for this study. The sample solutions were prepared as described above for the HPLC samples. Each sample was injected at 9 μL/min with a syringe pump. Mass spectrum was recorded for 1 minute. The molecular weight of PuraStat® (Ac-(RADA)$_4$-NH$_2$) (SEQ ID NO:1) is 1712, which matches its calculated molecular weight from the major three peaks at m/3=572, m/2=857, and m=1713 in all the spectra of control and irradiated PuraStat® samples.

The assigned peaks to Ac-RADARADARADARADA-NH$_2$ (SEQ ID NO:1) are,
 M/z=572=(Mw+3)/3, so the calculated Mw=1713
 M/z=857=(Mw+2)/2, so the calculated Mw=1712
 M/z=1713=Mw+1, so the calculated Mw=1712

The rheological properties of PuraStat® samples before and after gamma sterilization were evaluated using a rheometer (Discovery HR 1, TA Instruments) at 37° C. Flow tests were carried out with 20 mm plate-plate geometry and 800 μm of gap distance at a shear rate range of 0.001 1/sec to 3,000 1/sec at 37° C. Sample solution (350 μL) was placed on the rheometer plate and excess solution was gently removed; measurements were performed after 2 minutes of relaxation time at 37° C. The viscosity (h) was recorded from very low shear rate (0.001 1/sec) to high shear rate (3000 1/sec).

L929 neutral red uptake tests were performed to investigate the cytotoxicity of the irradiated PuraStat®. These tests were performed by Toxikon located in Bedford Mass., USA. The study was done based upon ISO 10993-5, 2009, Biological Evaluation of Medical Devices—Part 5: Tests for in Vitro Cytotoxicity and ISO 10993-12, 2012, Biological Evaluation of Medical Devices—Part 12: Sample Preparation and Reference Materials. The biological reactivity of a mammalian cell monolayers, L929 mouse fibroblasts, in response to the test article extract was determined. The test article extract was obtained with serum-supplemented Minimum Essential Medium (MEM) at the ratio 0.2 g of article per mL. Extraction was done for 24±2 hours at 37±1° C. Positive control (Natural Rubber) and negative control (Negative Control Plastic) articles and an untreated control (blank) were prepared to verify the proper functioning of the test system. The test article and control article extracts were used to replace the maintenance medium of the cell culture. The test article extract was tested at the 100% (neat) concentration. All cultures were incubated in at least 6 replicates for 24 to 26 hours at 37±1° C., in a humidified atmosphere containing 5±1% carbon dioxide ($CO_2$). The viability of cells following the exposure to the extracts was measured via their capacity to uptake a vital dye, Neutral Red. This dye was added to the cells to be actively incorporated in viable cells. The number of viable cells correlates to the color intensity determined by photometric measurements at 540 nm after extraction.

The viability of cells exposed to the negative control article and positive control article extracts needs to be greater than or equal to 70% and less than 70% of the untreated control, respectively, to confirm the validity of the assay. The test article meets the requirements of the test if the viability % is greater than or equal to 70% of the untreated control.

We tested only PuraStat® samples irradiated at the highest dose (i.e., 40 kGy) considering they represent all the irradiated samples, because they should have more effect, if any, on cytotoxicity than those irradiated at lower doses.

TABLE 20

Summary Table of Irradiation Sterilization Tests

| Testing conditions | Appearance | pH | HPLC and MS | Rheology | Cytotoxicity |
|---|---|---|---|---|---|
| PuraStat® (Control) | Clear and viscous | 2.2 | Control | Control | Not toxic |
| PuraStat® with Gamma at 25 kGy | Clear and viscous | 2.3 | ~5% degrade | — | — |
| PuraStat® with Gamma at 28k or 40 kGy | Clear and viscous | 2.3 | ~15% degrade | equivalent | Not toxic |

The amount of peptide prior to the irradiation. After up to 25 kGy of irradiation, PuraStat®'s degradation did not exceed 5% of the amount of peptide prior to the irradiation.

From the pattern of degradation of control PuraStat®, we found that degradation mainly occurs at the points between ~RAD and A~. From the additional pattern of degradation of Ac-(RADA)$_4$-NH$_2$ (SEQ ID NO:1) when PuraStat® is sterilized with irradiation, we found that irradiation can cause additional degradation at the point between ~R and AD~.

Overall, the rheological property of PuraStat® with gamma irradiation was equivalent to PuraStat® control. All the irradiated PuraStat® and PuraStat® control samples meet the requirements of the test and are not considered to have a cytotoxic potential.

Table 21 below shows results of HPLC tests was performed to evaluate the major peptide content of PuraStat® before (control) and after Gamma irradiation.

TABLE 21

The HPLC and LC-MS analysis for two Product Form HPLC and LCMS results in each peak

| PuraStat® current product (non-irradiated) | | | | | PuraStat® proposed product (irradiated) | | | | |
|---|---|---|---|---|---|---|---|---|---|
| HPLC | | | | LC-MS | HPLC | | | | LC-MS |
| Peak | $t_R$ | Area | Area % | Representative m/z | Peak | $t_R$ | Area | Area % | Representative m/z |
| 1 | 6.37 | 25.70 | 4.39 | 1329(666) | 1 | 6.35 | 8.20 | 1.90 | 1329(666) |
| 2 | 6.73 | 8.49 | 1.44 | 1229(615) | 2 | 6.73 | 2.90 | 0.67 | 1229(615) |
| 3 | 7.15 | 9.98 | 1.71 | 1300(651) | 3 | 7.27 | 12.00 | 2.78 | 1143(572) |
| 4 | 7.30 | 9.29 | 1.59 | 1143(572) 893 | 4 | 7.56 | 2.29 | 0.53 | 1671(836) |
| 5 | 7.75 | 4.75 | 0.81 | 1671(836), 1713(857) | 5 | 7.71 | 2.34 | 0.54 | 1671(836) |
| 6 | 8.01 | 7.49 | 1.28 | 1713(857), 750 | 6 | 7.90 | 7.62 | 1.77 | 1671(836), 1713(857) |
| 7 | 8.18 | 6.95 | 1.19 | 1643(823), 1713(857) | 7 | 8.16 | 4.06 | 0.94 | 1643(823), 1713(557), 1513 |
| 8 | 8.29 | 2.15 | 0.36 | 1643(823), 1713(857) | 8 | 8.27 | 7.95 | 1.84 | 1643(823), 1713(557), 1513 |
| 9 | 8.45 | 473.23 | 80.80 | 1713(857) | 9 | 8.47 | 348.78 | 80.89 | 1713(857) |
| 10 | 8.80 | 11.89 | 2.03 | 1557, 783, 857 | 10 | 8.77 | 12.95 | 3.00 | 1557, 783 |

TABLE 21-continued

The HPLC and LC-MS analysis for two Product Form
HPLC and LCMS results in each peak

| | PuraStat ® current product (non-irradiated) | | | | PuraStat ® proposed product (irradiated) | | | |
|---|---|---|---|---|---|---|---|---|
| | HPLC | | | LC-MS | HPLC | | | LC-MS |
| Peak | $t_R$ | Area | Area % | Representative m/z | Peak | $t_R$ | Area | Area % | Representative m/z |
| 11 | 8.93 | 4.54 | 0.77 | 783, 857 | 11 | | | | |
| 12 | 9.06 | 4.85 | 0.82 | 839, 1713(857) | 12 | 9.00 | 10.46 | 2.43 | 839, 1713(857) |
| 13 | 10.00 | 16.26 | 2.77 | 482, 839, 891 | 13 | 9.96 | 11.61 | 2.69 | 839, 482 |

Agilent HPLC 1100 (Agilent Technologies) was used for this study. Column temperature was kept at 25° C. Agilent Zorbax 300SB-C18 column (4.6 mm×250 mm, 5 mm, 300 Å) was used for this test. Solvent A was water with 0.1% TFA and solvent B was 80% Acetonitrile with 0.1% TFA. Gradient of solvent B was controlled from 10% to 40% in 20 min and 40% for another 5 min at 25° C. PuraStat® (40 mg) was mixed with 10 μL of DH$_2$O and 500 μL of formic acid and vortexed, and the mixture was mixed with DH$_2$O (4,450 μL) and vortexed. 20 mL of samples were injected using an Agilent autosampler. Results are shown in following Table 23.

TABLE 23

| | PuraStat ® control | PuraStat ® irradiated above 25 kGy |
|---|---|---|
| Major Peptide Content (n = 3) | 83.8 +/− 1% | 81.3 +/− 0.7% |
| Manufacturing Specification | 75% and more | |

Findings—Overall, the major peptide content of PuraStat® decreased with gamma irradiation methods and the extent of decrease was more significant with higher dose. After up to 40 kGy of irradiation, PuraStat®'s degradation did not exceed 15% of the amount of peptide prior to the irradiation. After up to 25 kGy of irradiation, PuraStat®'s degradation did not exceed 5% of the amount of peptide prior to the irradiation.

From the pattern of degradation of control PuraStat®, we found that degradation mainly occurs at the points between ~RAD and A~. From the additional pattern of degradation of Ac-(RADA)$_4$-NH$_2$ (SEQ ID NO:1) when PuraStat® is sterilized with irradiation, we found that irradiation can cause additional degradation at the point between ~R and AD~.

Overall, the rheological property of PuraStat® with gamma irradiation was equivalent to PuraStat® control. All the irradiated PuraStat® and PuraStat® control samples met the requirements of the test and were not considered to have a cytotoxic potential.

SEQUENCE LISTING

```
Sequence total quantity: 15
SEQ ID NO: 1            moltype = AA  length = 16
FEATURE                 Location/Qualifiers
REGION                  1..16
                        note = Description of Artificial Sequence: Synthetic peptide
MOD_RES                 1
                        note = N-term Acetylated
MOD_RES                 16
                        note = C-term Amidated
source                  1..16
                        mol_type = protein
                        organism = synthetic construct
REGION                  1..16
                        note = Synthetically produced
SEQUENCE: 1
RADARADARA DARADA                                                           16

SEQ ID NO: 2            moltype = AA  length = 12
FEATURE                 Location/Qualifiers
REGION                  1..12
                        note = Description of Artificial Sequence: Synthetic peptide
REGION                  1..12
                        note = Synthetically produced
MOD_RES                 12
                        note = C-term Amidated
MOD_RES                 1
                        note = N-term Acetylated
source                  1..12
                        mol_type = protein
                        organism = synthetic construct
```

-continued

```
SEQUENCE: 2
KLDLKLDLKL DL                                                    12

SEQ ID NO: 3         moltype = AA  length = 13
FEATURE              Location/Qualifiers
REGION               1..13
                     note = Description of Artificial Sequence: Synthetic peptide
REGION               1..13
                     note = Synthetically produced
MOD_RES              1
                     note = N-term Acetylated
MOD_RES              13
                     note = C-term Amidated
source               1..13
                     mol_type = protein
                     organism = synthetic construct
SEQUENCE: 3
IEIKIEIKIE IKI                                                   13

SEQ ID NO: 4         moltype = AA  length = 12
FEATURE              Location/Qualifiers
MOD_RES              1
                     note = N-term Acetylated
REGION               1..12
                     note = Synthetically produced
MOD_RES              12
                     note = C-term Amidated
source               1..12
                     mol_type = protein
                     organism = synthetic construct
REGION               1..12
                     note = Description of Artificial Sequence: Synthetic peptide
SEQUENCE: 4
QLELQLELQL EL                                                    12

SEQ ID NO: 5         moltype = AA  length = 5
FEATURE              Location/Qualifiers
REGION               1..5
                     note = Description of Artificial Sequence: Synthetic peptide
REGION               1..5
                     note = Synthetically produced
MOD_RES              5
                     note = C-term Amidated
source               1..5
                     mol_type = protein
                     organism = synthetic construct
SEQUENCE: 5
ARADA                                                            5

SEQ ID NO: 6         moltype = AA  length = 13
FEATURE              Location/Qualifiers
REGION               1..13
                     note = Description of Artificial Sequence: Synthetic peptide
REGION               1..13
                     note = Synthetically produced
MOD_RES              13
                     note = C-term Amidated
source               1..13
                     mol_type = protein
                     organism = synthetic construct
SEQUENCE: 6
ARADARADAR ADA                                                   13

SEQ ID NO: 7         moltype = AA  length = 16
FEATURE              Location/Qualifiers
REGION               1..16
                     note = Description of Artificial Sequence: Synthetic peptide
REGION               1..16
                     note = Synthetically produced
MOD_RES              16
                     note = C-term Amidated
source               1..16
                     mol_type = protein
                     organism = synthetic construct
SEQUENCE: 7
RADARADARA DARADA                                                16

SEQ ID NO: 8         moltype = AA  length = 9
FEATURE              Location/Qualifiers
```

```
REGION              1..9
                    note = Description of Artificial Sequence: Synthetic peptide
REGION              1..9
                    note = Synthetically produced
MOD_RES             9
                    note = C-term Amidated
source              1..9
                    mol_type = protein
                    organism = synthetic construct
SEQUENCE: 8
ARADARADA                                                                        9

SEQ ID NO: 9        moltype = AA  length = 11
FEATURE             Location/Qualifiers
REGION              1..11
                    note = Description of Artificial Sequence: Synthetic peptide
REGION              1..11
                    note = Synthetically produced
MOD_RES             11
                    note = C-term Amidated
source              1..11
                    mol_type = protein
                    organism = synthetic construct
SEQUENCE: 9
ADARADARAD A                                                                    11

SEQ ID NO: 10       moltype = AA  length = 11
FEATURE             Location/Qualifiers
REGION              1..11
                    note = Description of Artificial Sequence: Synthetic peptide
REGION              1..11
                    note = Synthetically produced
source              1..11
                    mol_type = protein
                    organism = synthetic construct
SEQUENCE: 10
ARADARADAR A                                                                    11

SEQ ID NO: 11       moltype = AA  length = 11
FEATURE             Location/Qualifiers
REGION              1..11
                    note = Description of Artificial Sequence: Synthetic peptide
REGION              1..11
                    note = Synthetically produced
MOD_RES             1
                    note = N-term Acetylated
source              1..11
                    mol_type = protein
                    organism = synthetic construct
SEQUENCE: 11
RADARADARA D                                                                    11

SEQ ID NO: 12       moltype = AA  length = 15
FEATURE             Location/Qualifiers
REGION              1..15
                    note = Description of Artificial Sequence: Synthetic peptide
REGION              1..15
                    note = Synthetically produced
MOD_RES             15
                    note = C-term Amidated
source              1..15
                    mol_type = protein
                    organism = synthetic construct
SEQUENCE: 12
ADARADARAD ARADA                                                                15

SEQ ID NO: 13       moltype = AA  length = 15
FEATURE             Location/Qualifiers
REGION              1..15
                    note = Description of Artificial Sequence: Synthetic peptide
REGION              1..15
                    note = Synthetically produced
MOD_RES             1
                    note = N-term Acetylated
source              1..15
                    mol_type = protein
                    organism = synthetic construct
SEQUENCE: 13
RADARADARA DARAD                                                                15
```

```
SEQ ID NO: 14          moltype = AA  length = 7
FEATURE                Location/Qualifiers
REGION                 1..7
                       note = Description of Artificial Sequence: Synthetic peptide
REGION                 1..7
                       note = Synthetically produced
MOD_RES                1
                       note = N-term Acetylated
source                 1..7
                       mol_type = protein
                       organism = synthetic construct
SEQUENCE: 14
RADARAD                                                                            7

SEQ ID NO: 15          moltype = AA  length = 5
FEATURE                Location/Qualifiers
REGION                 1..5
                       note = Description of Artificial Sequence: Synthetic peptide
REGION                 1..5
                       note = Synthetically produced
MOD_RES                1
                       note = N-term Acetylated
source                 1..5
                       mol_type = protein
                       organism = synthetic construct
SEQUENCE: 15
RADAR                                                                              5
```

The invention claimed is:

1. A sterilized solution of self-assembling peptide (SAP) made by sterilizing a self-assembling peptide (SAP) solution, the method of sterilization comprising:
   (a) placing one or more containers with the solution of self-assembling peptide into an irradiation machine, said self-assembling peptide selected from the group consisting of RADA16 (SEQ ID NO:1), KLD12 (SEQ ID NO:2), and IEIK13 (SEQ ID NO:3), and capable of forming a hydrogel when applied to a biological tissue at about neutral pH; and
   (b) exposing the one or more containers to gamma ray, X-ray, and/or e-beam irradiation at a predetermined dose so that the self-assembling peptide solution is sterilized to a pre-determined Sterility Assurance Level (SAL) without substantial degradation of the peptide wherein the concentration of the degradation products of a full-length peptide in the solution post-irradiation ranges from 0.1% to 5% w/v while its desired biological or physical properties are maintained substantially at the same level or improved;
   wherein the desired biological or physical properties are selected from the group consisting of: hemostatic, anti-adhesion, prevention of re-bleeding, anti-stenosis, tissue occlusion, mucosa elevation, wound healing, storage modulus, viscosity, and tissue void filling property.

2. The self-assembling peptide solution of claim 1, wherein the dose is 15-50 kGy.

3. The self-assembling peptide solution of claim 2, wherein the solution is irradiated by X-ray or e-beam.

4. The self-assembling peptide solution of claim 1, wherein the peptide solution contains about 2.5% w/v of RADA16 (SEQ ID NO:1), and the dose is 15-24 kGy.

5. The self-assembling peptide solution of claim 1, wherein the amount of total peptides that are degraded after the irradiation does not exceed 20% by weight of the amount of the self-assembling peptide prior to the irradiation.

6. The self-assembling peptide solution of claim 5, wherein the pre-irradiation bioburden of the self-assembling peptide solution is 9 CFU or less.

7. The self-assembling peptide solution of claim 1, wherein irradiation dose achieves sterility assurance level (SAL) of at least $10^{-6}$.

8. The self-assembling peptide solution of claim 1, wherein the pH of the solution pre- and post-irradiation ranges from about 1.8 to 3.5.

9. The self-assembling peptide solution of claim 1, wherein the one or more containers is/are a plastic syringe(s).

10. The self-assembling peptide solution of claim 1, wherein the storage modulus of the gelled solution is increased at least by 10% post-irradiation.

11. The self-assembling peptide solution of claim 1, wherein the self-assembling peptide solution is subjected to shearing post-irradiation to reduce or restore its storage modulus.

12. The self-assembling peptide solution of claim 1, wherein the SAP solution exhibits a post-irradiation mass spectrometric (MS) profile having major $M_z$ peaks at 836/1670, 1100, and 1513 m/z.

* * * * *